US007993879B2

(12) United States Patent
Tsien et al.

(10) Patent No.: US 7,993,879 B2
(45) Date of Patent: *Aug. 9, 2011

(54) FLUORESCENT PROTEIN SENSORS FOR DETECTION OF ANALYTES

(75) Inventors: Roger Y. Tsien, La Jolla, CA (US); Atsushi Miyawaki, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 204 days.

This patent is subject to a terminal disclaimer.

(21) Appl. No.: 11/334,622

(22) Filed: Jan. 17, 2006

(65) Prior Publication Data

US 2006/0112440 A1    May 25, 2006

Related U.S. Application Data

(63) Continuation of application No. 09/554,000, filed on Apr. 20, 2000, now Pat. No. 7,060,869, which is a continuation of application No. 08/818,252, filed on Mar. 14, 1997, now Pat. No. 6,197,928.

(51) Int. Cl.
*C07K 1/00* (2006.01)
(52) U.S. Cl. ....... 435/69.7; 530/350; 536/23.4; 436/546
(58) Field of Classification Search .................. None
See application file for complete search history.

(56) References Cited

U.S. PATENT DOCUMENTS

| | | | |
|---|---|---|---|
| 4,868,103 A | 9/1989 | Stavrianopoulos et al. | |
| 5,134,232 A | 7/1992 | Tsien et al. | |
| 5,439,797 A | 8/1995 | Tsien et al. | |
| 5,981,200 A | 11/1999 | Tsien et al. | |
| 5,998,204 A | 12/1999 | Tsien et al. | |
| 6,197,928 B1 * | 3/2001 | Tsien et al. | 530/350 |
| 6,803,188 B1 * | 10/2004 | Tsien et al. | 435/6 |
| 7,060,869 B2 | 6/2006 | Tsien et al. | |
| 2002/0164674 A1 | 11/2002 | Tsien et al. | |

FOREIGN PATENT DOCUMENTS

| | | |
|---|---|---|
| EP | 0 428 000 | 10/1990 |
| WO | WO 91/01305 | 2/1991 |
| WO | WO 94/28166 | 12/1994 |
| WO | WO 94/28173 | 12/1994 |
| WO | WO 95/07463 | 3/1995 |
| WO | WO 95/21191 | 8/1995 |
| WO | WO 96/13607 | 5/1996 |
| WO | WO 96/23810 | 8/1996 |
| WO | WO 96/23898 | 8/1996 |
| WO | WO 96/27027 | 9/1996 |
| WO | WO 96/27675 | 9/1996 |
| WO | WO 97/11094 | 3/1997 |
| WO | WO 97/28261 | 8/1997 |
| WO | WO 98/02571 | 1/1998 |
| WO | WO 98/06737 | 2/1998 |

OTHER PUBLICATIONS

Office Action mailed May 4, 2009 in U.S. Appl. No. 10/057,505.
Baldwin et al., "Cloning and Expression of the *lux*Y Gene from *Vibrio fischeri* Strain Y-1 in *Escherichia coli* and Complete Amino Acid Sequence of the Yellow Fluorescent Protein," *Biochemistry*, 29:5509-5515 (1990).
Blondel and Bedouelle, "Engineering the quaternary structure of an exported protein with a leucine zipper," *Protein Engineering*, 4(4):457-461(1991).
Bouvier et al., "Leishmanolysin: Surface Metalloproteinase of *Leishmania*," *Metallopeptidases, The Zn-Endopeptidase of Leishmania*, 614-633 (1995).
Cartwright et al., "Use of β-Lactamase as a Secreted Reporter of Promoter Function in Yeast," *Yeast*, 10:497-508 (1994).
Cesare, T., "Functional consequences of Na/Ca exchanger overexpression in cardiac myocytes," *Ann. New York Acad. Sci.*, 976:520-527 (2002).
Chalfie et al., "Green Fluorescent Protein as a Marker for Gene Expression," *Science*, 263:802-805 (1994).
Cheng et al., "Use of green fluorescent protein variants to monitor gene transfer and expression in mammalian cells," *Nature Biotechnology*, 14:606-609 (1996).
Cody et al., "Chemical Structure of the Hexapeptide Chromophore of the *Aequorea* Green-Fluorescent Protein," *Biochemistry*, 32:1212-1218 (1993).
Cormack, B.P., et. al.: Cloning vector pEGFP-N2 with enhanced green fluorescent protein gene, complete sequence, retrieved from EBI Database accession No. CV57608 XP002243579.
Cubitt et al., "Understanding, improving and using green fluorescent proteins," *TIBS 20*, 448-455(1995).
Delagrave et al., "Red-Shifted Excitation Mutants of the Green Fluorescent Protein," *Bio/Technology*, 13:151-154 (1995).
Deschamps et al., "Rapid Purification of Recombinant Green Fluorescent Protein Using the Hydrophobic Properties of an HPLC Size-Exclusion Column," *Protein Expression and Purification*, 6:555-558 (1995).
Dunn et al., "Subsite Preferences of Retroviral Proteinases," *Substrate Specificity and Inhibitor Design, Subsite Preferences*, 254-279 (1994).
Ehrig et al., "Green-fluorescent protein mutants with altered fluorescence excitation spectra" FEBS Letters. vol. 367, Issue 2, Jun. 26, 1995, pp. 163-166.
Geoghegan et al., "Site-Directed Double Fluorescent Tagging of Human Renin and Collagenase (MMP-1) Substrate Peptides Using the Periodate Oxidation of N-Terminal Serine. An Apparently General Strategy for Provision of Energy-Transfer Substrates for Proteases," *Bioconjugate Chem.*, 4:537-544 (1993).

(Continued)

*Primary Examiner* — Zachariah Lucas
*Assistant Examiner* — Michelle Horning
(74) *Attorney, Agent, or Firm* — Morgan, Lewis & Bockius LLP

(57) ABSTRACT

Fluorescent indicators including a binding protein moiety, a donor fluorescent protein moiety, and an acceptor fluorescent protein moiety are described. The binding protein moiety has an analyte-binding region which binds an analyte and causes the indicator to change conformation upon exposure to the analyte. The donor moiety and the acceptor moiety change position relative to each other when the analyte binds to the analyte-binding region. The donor moiety and the acceptor moiety exhibit fluorescence resonance energy transfer when the donor moiety is excited and the distance between the donor moiety and the acceptor moiety is small. The indicators can be used to measure analyte concentrations in samples, such as calcium ion concentrations in cells.

22 Claims, 18 Drawing Sheets

OTHER PUBLICATIONS

Giuliano and Post, "Fluorescent Protein Biosensors: Measurement of Molecular Dynamics in Living Cells," *Annual Review of Biophysics and Biomolecular Structure*, 24:405-34 (1995).

Graff et al., "Protein Kinase C Substrate and Inhibitor Characteristics of Peptides Derived from the Myristoylated Alanine-rich C Kinase Substrate (MARCKS) Protein Phosphorylation Site Domain," *The Journal of Biological Chemistry*, 266(2):14390-14398 (1991).

Hardy et al., "Genetic Variability and Alzheimer's Disease," *Amyloid Protein Precursor in Development, Aging and Alzheimer's Disease*, 190-198 (1994).

Heim and Tsien, "Engineering green fluorescent protein for improved brightness, longer wavelengths and fluorescence resonance energy transfer," *Current Biology*, 6(2):178-182 (1996).

Heim et al., "Improved green fluorescence," *Nature*, 373:663-664 (1995).

Heim et al., "Wavelength mutations and postttanslational autoxidation of green fluorescent protein," *Biochemistry*, 91:12501-12504 (1994).

Houdebine, L.-M., "Production of pharmaceutical proteins from transgenic animals," *J. Biotech.*, 34:269-287 (1994) (abstract provided).

Inouye and Tsuji, "*Aequorea* green fluorescent protein Expression of the gene and fluorescence characteristics of the recombinant protein," *FEBS Letters*, 341:277-280 (1994).

Kain et al., "Green Fluorescent Protein as a Reporter of Gene Expression and Protein Localization, "*BioTechniques*, 19(4):650-655 (1995).

Kappel, C.A., et al., "Regulating gene expression in transgenic animals," *Curr. Opin. Biotech.*, 3:548-553 (1992) (abstract provided).

Kemp and Pearson, "Protein kinase recognition sequence motifs," *TIBS 15*, 342-346 (1990).

Knight, C. Graham, "Fluorimetric Assays of Proteolytic Enzymes," *Methods in Enzymology, Proteolytic Enzymes: Aspartic and Metallo Peptidases*, 248:18-34 (1995).

Krafft and Wang, "Synthetic Approaches to Continuous Assays of Retroviral Proteases," *Methods in Enzymology*, 241:70-86 (1994).

Lee et al., "A requirement of hydrophobic and basic amino acid residues for substrate recognition by $Ca^{2+}$/calmodulin-dependent protein kinase la," *Pro. Natl. Acad Sci.*, 91:6413-6417 (1994).

Levine and Ward, "Isolation and Characterization of a Photoprotein, "Phialidin", and a Spectrally Unique Green-Fluorescent Protein From the Bioluminescent Jellyfish *Phialidium gregarium*", *Comparative Biochemistry and Physiology Part B*: Comparative vol. 72, Issue 1, 1982, pp. 77-85.

Matayoshi et al., "Novel Fluorogenic Substrates for Assaying Retroviral Proteases by Resonance Energy Transfer," *Science*, 247:954-958 (1990).

Mitra et al., "Fluorescence resonance energy transfer between blue-emitting and red-shifted excitation derivatives of the green fluorescent protein," *Gene*, 173:13-17 (1996).

Muhlrad et al., "A Rapid Method for Localized Mutagenesis of Yeast Genes," *Yeast*, 8:79-82 (1992).

Mullins, L. J., and J. J. Mullins, "Perspective series: Molecular medicine in genetically engineered animals," *J. Clin. Invest.*, 98(11):S37-S40 (1996).

Mullins, L. J., and J. J. Mullins, "Transgenesis in the Rat and Larger Mammals" *J. Clin. Invest.*, Apr. 1996; 97 (7): 1557-1560 (1996).

Murray, J. D., "Genetic modification of animals in the next century," *Theriogenol,*, 51(1):149-159 (1999).

Norris and Miller, "Nucleotide sequence of a cDNA clone encoding the precursor of the peridinin-chlorophyll a-binding protein from the dinoflagellate *Symbiodinium* sp.," *Plant Molecular Biology*, 24:673-677 (1994).

Prasher et al., "Primary structure of the *Aequorea victoria* green-fluorescent protein," *Gene*, 111:229-233 (1992).

Pursel, V. G., et al., "Expression and performance in transgenic pigs," *J. Reproduct. Fertil. Suppl.*, 40:235-245 (1990).

Richards, C. A., and B. E. Huber, "Generation of a transgenic model for retrovirus-mediated gene therapy for hepatocellular carcinoma is thwarted by the lack of transgene expression," *Human Gene Therapy*, 4(2):143-150 (1993).

Roth, Amy F., "Purification and Protease Susceptibility of the Green-Fluorescent protein of *Aequorea aequorea* with a Note on *Halistaura,"* Dissertation submitted to the Graduate School-New Brunswick, Rutgers, The State University of New Jersey, 1995.

Sala-Newby and Campbell, "Engineering a bioluminescent indicator for cyclic AMP-dependent protein kinase," *Biochem.*, 279:727-732 (1991).

Seidah and Chretien, "Pro-Protein Convertases of Subtilisin/Kexin Family," *Serine Peptidases, Mammalian Prohormone Convertases*, 175-188, Methods Enzymol. 1994; 244:175-88.

Sigmund, C. D., "Viewpoint: are studies in genetically altered mice out of control?", *Arterioscler. Thromb. Vasc. Biol.*, 20(6):1425-1429 (2000).

Smith et al., "Purification and Kinetic Characterization of Human Cytomegalovirus Assemblin," *Serine Peptidases, Human Cytomegalovirus Assemblin*, 412-423 (1994).

Songyang et al., "Use of an oriented peptide library to determine the optimal substrates of protein kinases," *Current Biology*, 4(11):973-982 (1994).

Stokoe et al., "The substrate specificity and structure of mitogen-activated protein (MAP) kinase-activated protein kinase-2," 296:843-849 (1993).

Stryer, Lubert, "Fluorescence Energy Transfer as a Spectroscopic Ruler," *Annual Review of Biochemistry*, 47:819-46 (1978).

Thornberry, Nancy A., "Interleukin-1β Converting Enzyme," *Cysteine Peptidases Interleukin-1β Converting Enzyme*, 615-631, *Protein Sci.* Jan. 1995;4(1):3-12.

Tsien et al., "FRET for studying intracellular signaling," *Trends in Cell Biology*, 3:242-245 (1993).

Wall, R. J., "Transgenic livestock: progress and prospects fo the future," *Theriogenol.*, 45:57-68 (1996).

Wall, R. J., et al., "Transgenic dairy cattle: genetic engineering on a large scale," *J. Dairy Sci.*, 80:2213-2224 (1997).

Wall, R.J., "Transgenic livestock: Progress and prospects for the future," *Theriogenol.*, 45:57-68 (1996) (abstract provided).

Ward and Bokman, "Reversible Denaturation of *Aequorea* Green-Fluorescent Protein: Physical Separation and Characterization of the Renatured Protein," *Biochemistry*, 21:4535-4540 (1982).

Ward et al., "Sequence and Chemical Structure of the Hexapeptide Chromophore of *Aequorea* Green-Fluorescent Protein," *Photochem., Photobiol.*, 49:25S (1989).

Ward et al., "Spectral Perturbations of the *Aequorea* Green-Fluorescent Protein," *Photochem. Photobiol.*, 35:803-808 (1982).

Ward, William W., "Properties of the Coelenterate Green-Fluorescent Proteins," *Bioluminescence and Chemiluminescence Basic Chemistry and Analytical Applications*, 235-242 (1981).

Wilbanks and Glazer, "Rod Structure of a Phycoerythrin-II-containing Phycobilisome, Organization and Sequence of the Gene Cluster Encoding the Major Phycobiliprotein Rod Components in the Genome of Marine *Synechococcus* SP," *The Journal of Biological Chemistry*, 268(2):1226-1235 (1993).

Wu and Brand, "Review Resonance Energy Transfer: Methods and Applications," *Analytical Biochemistry*, 218:1-13 (1994).

Yaron et al., "Intramolecularly Quenched Fluorogenic Substrates for Hydrolytic Enzymes," *Analytical Biochemistry*, 95:228-235 (1979).

\* cited by examiner (SEQ ID. NO:1)
ATGGTGAGCAAGGGCGAGGAGCTGTTCACCGGGGTGGTGCCCATCCTGGTCGAGCTGGACGGCGA
CGTAAACGGCCACAAGTTCAGCGTGTCCGGCGAGGGCGAGGGCGATGCCACCTACGGCAAGCTGA
CCCTGAAGTTCATCTGCACCACCGGCAAGCTGCCCGTGCCCTGGCCCACCCTCGTGACCACCCTG
ACCCATGGCGTGCAGTGCTTCAGCCGCTACCCCGACCACATGAAGCAGCACGACTTCTTCAAGTC
CGCCATGCCCGAAGGCTACGTCCAGGAGCGCACCATCTTCTTCAAGGACGACGGCAACTACAAGA
CCCGCGCCGAGGTGAAGTTCGAGGGCGACACCCTGGTGAACCGCATCGAGCTGAAGGGCATCGAC
TTCAAGGAGGACGGCAACATCCTGGGGCACAAGCTGGAGTACAACTTCAACAGCCACAACGTCTA
TATCATGGCCGACAAGCAGAAGAACGGCATCAAGGTGAACTTCAAGATCCGCCACAACATCGAGG
ACGGCAGCGTGCAGCTCGCCGACCACTACCTGAGCACCCAGTCCGCCCTGAGCAAAGACCCCAAC
GAGAAGCGCGA
CTGCCCGACAACCACTACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCATGGACGAGCTGTACA
TTGCAGAGTTCAAAGAAGCCTTCTCATTATTCGACAAGGATGGGAGCGGCCATCACCACAAAG
GAACTTGGCACCGTTATGAGGTCGCTTGGACAAAACCCAACGGAAGCAGAATTGCAGGATATGAT
CAATGAAGTCGATGCTGATGGCAATGGAACGATTTACTTTCCTGAATTTCTTACTATGATGGCTA
GAAAAATGAAGGACACAGACGGAAGAGGAAATCCGAGAAGCATTCCGTGTTTTTGACAAGGAT
GGGAACGGCTACATCAGCGCTGCTGAATTACGTCACGTCATGACAAACCTCGGGGAGAAGTTAAC
AGATGAAGAAGTTGATGAAATGATAAGGAAGCAGATATCGATGGTGATGCCAAGTAAACTATG

*FIG. 7-1*

(SEQ ID. NO:1)
AAGAGTTTGTACAAATGATGACAGCAAAGGGGGGAAGAGAGGCGCTGGAAGAGAAAACTTCATTGCC
GTCAGCGCTGCCAACCGGTTCAAGAAGATCTCCGAGCTCATGGTGAGCTAAGGGCGAGGAGCTGTT
CACCGGGGTGTGCCCATCCTGTGAGCGGACGGCGACGTAAACGGCCACAAGTTCAGCGGTGT
CCGGGCGAGGGCGAGGGCGATGCCACCTACGGCCAAGCTGACCCTGAAGTTCATCTGCACCACCGGC
AAGCTGCCCGTGCCCTGGCCCACCCTCGTGACCACCCTGACCCTACGGCGTGCAGTGCTTCAGCCG
CTACCCCGACCACATGAAGCAGCACGACTTCTTCAAGTCCGCCATGCCCGAAGGCTACGTCCAGG
AGGGCACCATCTTCTTCAAGGACGACGGCAACTACAAGACCCGCGCGAGGTGAAGTTCGAGGGC
GACACCCTGGTGAACCGCATCGAGCTGAAGGGCATCGACTTCAAGGAGGACGGCAACATCCTGGG
GCACAAGCTGGAGTACAACTACAACAGCCACAACGTCTATATCATGGCCGACAAGCAGAAGAACG
GCATCAAGGTGAACTTCAAGATCCGCCACAACATCGAGGACGGCAGCGTGCAGCTCGCCGACCAC
TACCAGCAGAACACCCCCATCGGCGATGGCCCCGTGCTGCTGCCCGACAACCACTACCTGAGCAC
CCAGTCCGCCCTGAGCAAAGACCCCAACGAGAAGCGCGATCACATGGTCCTGCTGGAGTTCGTGA
CCGCCGCCGGGATCACTCTCGGCATGGACGAGCTGTACAAGTAA

*FIG. 7-2*

(SEQ ID. NO:2)
MVSKGEELFTGVVPILVELDGDVNGHKFSVSGEGEGDATYGKLTLKFICTTGKLPVPWPTLVTTL
THGVQCFSRYPDHMKQHDFFKSAMPEGYVQERTIFFKDDGNYKTRAEVKFEGDTLVNRIELKGID
FKEDGNILGHKLEYNFNSHNVYIMADKQKNGIKVNFKIRHNIEDGSVQLADHYQQNTPIGDPVL
LPDNHYLSTQSALSKDPNEKRDHMVLLEFVTAARMHDQLTEEQIAEFKEAFSLFDKDGDGTITTK
ELGTVMRSLGQNPTEAELQDMINEVDADGNGTIYFPEFLTMMARKMKDTDSEEEIREAFRVFDKD
GNGYISAAELRHVMTNLGEKLTDEEVDEMIREADIDGDGQVNYEEFVQMMTAKGGKRWKKNFIA
VSAANRFKKISELMVSKGEELFTGVVPILVELDGDVNGHKFSVSGEGEGDATYGKLTLKFICTTG
KLPVPWPTLVTTLTYGVQCFSRYPDHMKQHDFFKSAMPEGYVQERTIFFKDDGNYKTRAEVKFEG
DTLVNRIELKGIDFKEDGNILGHKLEYNYNSHNVYIMADKQKNGIKVNFKIRHNIEDGSVQLADH
YQQNTPIGDGPVLLPDNHYLSTQSALSKDPNEKRDHMVLLEFVTAAGITLGMDELYK*

FIG. 7-3

(SEQ ID. NO:3)
ATGGTGAGCAAGGGCGAGGAGCTGTTCACCGGGGTGGTGCCCATCCTGGTCGAGCTGGACGGCGA
CGTAAACGGCCACAAGTTCAGCGTGTCCGGCGAGGGCGAGGGCGATGCCACCTACGGCAAGCTGA
CCCTGAAGTTCATCTGCACCACCGGCAAGCTGCCCGTGCCCTGGCCCACCCTCGTGACCACCCTG
ACCCATGGCGTGCAGTGCTTCAGCCGCTACCCCGACCACATGAAGCAGCACGACTTCTTCAAGTC
CGCCATGCCCGAAGGCTACGTCCAGGAGCGCACCATCTTCTTCAAGGACGACGGCAACTACAAGA
CCCGCGCCGAGGTGAAGTTCGAGGGCGACACCCTGGTGAACCGCATCGAGCTGAAGGGCATCGAC
TTCAAGGAGGACGGCAACATCCTGGGGCACAAGCTGGAGTACAACTTCAACAGCCACAACGTCTA
TATCATGGCCGACAAGCAGAAGAACGGCATCAAGGTGAACTTCAAGATCCGCCACAACATCGAGG
ACGGCAGCGTGCAGCTCGCCGACCACTACCAGCAGAACACCCCCATCGGCGACGGCCCCGTGCTG
CTGCCCGACAACCACTACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCATGGACGAGCTGTACAAG
TTGCAGAGTTCAAAGAAGCCTTCTCATTATTCGACAAGGATGGGACGGCACCATCACCACAAG
GAACTTGGCACCGTTATGAGGTCGCTTGGACAAAACCAAGGAAGCAGAATTGCAGGATATGAT
CAATGAAGTCGATGCTGATGGCAATGGAACGATTACTTCCTGAATTTCTTACTATGATGGCTA
GAAAAATGAAGACACAGAGAGGAAGAGAATCCGAGAAGCATTCCGTGTTTTTGACAAGGAT
GGGAACGGCTACATCAGCGCTGCTGAATTAGTCAGTCAGTCATGACAAACCTCGGGAGAAGTTAAC
AGATGAAGAAGTTGATGAAATGATAAGGAAGCAGATATGATGGTGATGGCCAAGTAAACTATG

FIG. 8-1

(SEQ ID. NO:3)

AAGAGTTTGTACAAATGATGACAGCAAAGGGGGAAGAGAGGCGCTGAAGAAAACTTCATTGCC
GTCAGGGCTGCCAACCGGTTCAAGAAGATCTCCGAGCTCATGGTGAGCAAGGGCGAGGAGCTGTT
CACCGGGGTGGTGCCCATCCTGGTCGAGCTGGACGGCGAGTAAACGGCCACAAGTTCAGCGTGT
CCGGCGAGGGCGAGGGCGATGCCACCTACGGCAAGCTGACCCTGAAGTTCATCTGCACCACCGGC
AAGCTGCCCGTGCCCTGGCCCACCCTCGTGACCACCCTGACCTACGGCGTGCAGTGCTTCAGCCG
CTACCCCGACCACCATGAAGCAGCACGACTTCTTCAAGTCCGCCGAAGGCTACGTCCAGG
AGGGCACCATCTTCTTCAAGGACGACGGCAATGAGCGGCATCGAGCTGAAGGGCATCGACTTCAAGGAGGACGGCAACATCCTGGG
GCACAAGCTGGAGTACAACTACAACAGCCACAACGTCTATATCATGGCCGACAAGCAGAAGAACG
GCATCAAGGTGAACTTCAAGATCCGCCACAACATCGAGGACGGCAGCGTGCAGCTCGCCGACCAC
TACCAGCAGAACACCCCCATCGGCGACGGCCCCGTGCTGCTGCCCGACAACCACTACCTGAGCAC
CCAGTCCGCCCTGAGCAAAGACCCCAACGAAGAAGCGCGATCACATGGTCCTGCTGGAGTTCGTGA
CCGCCGCCGGGATCACTCTCGGCATGGACGAGCTGTACAAGCCAAAAAGAGAAGAAGGTGGAA
GACGCTTAA

*FIG. 8-2*

(SEQ ID. NO: 4)
MVSKGEELFTGVVPILVELDGDVNGHKFSVSGEGEGDATYGKLTLKFICTTGKLPVPWPTLVTTL
THGVQCFSRYPDHMKQHDFFKSAMPEGYVQERTIFFKDDGNYKTRAEVKFEGDTLVNRIELKGID
FKEDGNILGHKLEYNFNSHNVYIMADKQKNGIKVNFKIRHNIEDGSVQLADHYQQNTPIGDPVL
LPDNHYLSTQSALSKDPNEKRDHMVLLEFVTAARMHDQLTEEQIAEFKEAFSLFDKDGDGTITTK
ELGTVMRSLGQNPTEAELQDMINEVDADGNGTIYFPEFLTMMARKMKDTDSEEIREAFRVFDKD
GNGYISAAELRHVMTNLGEKLTDEEVDEMIREADIDGDGQVNYEEFVQMMTAKGGKRRWKKNFIA
VSAANREKKISEIMVSKGEELFTGVVPILVELDGDVNGHKFSVSGEGEGDATYGKLTLKFICTTG
KLPVPWPTLVTTLTYGVQCFSRYPDHMKQHDFFKSAMPEGYVQERTIFFKDDGNYKTRAEVKFEG
DTLVNRIELKGIDFKEDGNILGHKLEYNYNSHNVYIMADKQKNGIKVNEKIRHNIEDGSVQLADH
YQQNTPIGDGPVLLPDNHYLSTQSALSKDPNEKRDHMVLLEFVTAAGITLGMDELYKPKKKRKVE
DA*

*FIG. 8-3*

(SEQ ID. NO:5)
ATGGTGAGCAAGGGCGAGGAGCTGTTCACCGGGGTGGTGCCCATCCTGGTCGAGCTGGACGGCGA
CGTAAACGGCCACAAGTTCAGCGTGTCCGGCGAGGGCGAGGGCGATGCCACCTACGGCAAGCTGA
CCCTGAAGTTCATCTGCACCACCGGCAAGCTGCCCGTGCCCTGGCCCACCCTCGTGACCACCCTG
ACCCATGGCGTGCAGTGCTTCAGCCGCTACCCCGACCACATGAAGCAGCACGACTTCTTCAAGTC
CGCCATGCCCGAAGGCTACGTCCAGGAGCGCACCATCTTCTTCAAGGACGACGGCAACTACAAGA
CCCGCGCCGAGGTGAAGTTCGAGGGCGACACCCTGGTGAACCGCATCGAGCTGAAGGGCATCGAC
TTCAAGGAGGACGGCAACATCCTGGGGCACAAGCTGGAGTACAACTTCAACAGCCACAACGTCTA
TATCATGGCCGACAAGCAGAAGAACGGCATCAAGGTGAACTTCAAGATCCGCCACAACATCGAGG
ACGGCAGCGTGCAGCTCGCCGACCACTACCAGCAGAACACCCCCATCGGCGACGGCCCCGTGCTG
CTGCCCGACAACCACTACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCATGGACGAGCTGTACAAG
TTGCAGAGTTCAAAGAAGCCTTCTCATTATTCGACAAAACCCAAGGAAGCAGCAGAATTGCAGGATATGAT
GAACTTGGCACCGTTATGAGTCGCTTGGACAAAACCCAAGGAAGCAGCAGAATTGCAGGATATGAT
CAATGAGTCGATGCTGATGCAATGAACAGCGAAGAAGAGATTACTTCCTGAATTTCTTACTATGATGGCTA
GAAAAATGAAGGACACAGACAGCGAAGAGGAAATCCGAGAAGCATTCCGTGTTTTGACAAGGAT
GGGAACGGCTACATCAGCCCTGCTCAGTTACGTCAGTCATGACAAACCTCGGGGAGAAGTTAAC
AGATGAAGAAGTTGATGAATGATAAGGCAGCAGATATCGATGGTGATGGCCAAGTAAACTATG
FIG. 9-1

(SEQ ID. NO:5)

AAGAGTTTGTACAAATGATGACAGCAAAGGGGGAAGAGGCGCTGGAAGAAAAACTTCATTGCC
GTCAGCGCTGCCAACCGGTTCAAGAAGATCTCCGAGCTCATGGTGAGCAAGGGCGAGGAGCTGTT
CACCGGGGTGGTGCCCATCCTGGTCGAGCTGGACGGCGACGTAAACGGCCACAAGTTCAGCGTGT
CCGGCGAGGGCGAGGGCGATGCCACCTACGGCAAGCTGACCCTGAAGTTCATCTGCACCACCGGC
AAGCTGCCCGTGCCCTGGCCCACCCTCGTGACCACCCTGACCTACGGCGTGCAGTGCTTCAGCCG
CTACCCCGACCACATGAAGCAGCACGACTTCTTCAAGTCCGCCATGCCCGAAGGCTACGTCCAGG
AGCGCACCATCTTCTTCAAGGACGACGGCAACTACAAGACCCGCGCCGAGGTGAAGTTCGAGGGC
GACACCCTGGTGAACCGCATCGAGCTGAAGGGCATCGACTTCAAGGAGGACGGCAACATCCTGGG
GCACAAGCTGGAGTACAACTACAACAGCCACAACGTCTATATCATGGCCGACAAGCAGAAGAACG
GCATCAAGGTGAACTTCAAGATCCGCCACAACATCGAGGACGGCAGCGTGCAGCTCGCCGACCAC
TACCAGCAGAACACCCCCATCGGCGACGGCCCCGTGCTGCTGCCCGACAACCACTACCTGAGCAC
CCAGTCCGCCCTGAGCAAAGACCCCAACGAGAAGCGGGATCACATGGTCCTGCTGGAGTTCGTGA
CCGCCGCCGGGATCACTCTCGGCATGGACGAGCTGTACAAGTAA

FIG. 9-2

(SEQ ID. NO: 6)
MVSKGEELFTGVVPILVELDGDVNGHKFSVSGEGEGDATYGKLTLKFICTTGKLPVPWPTLVTTL
THGVQCFSRYPDHMKQHDFFKSAMPEGYVQERTIFFKDDGNYKTRAEVKFEGDTLVNRIELKGID
FKEDGNILGHKLEYNFNSHNVYIMADKQKNGIKVNFKIRHNIEDGSVQLADHYQQNTPIGDPVL
LPDNHYLSTQSALSKDPNEKRDHMVLLEFVTAAGITLGMDELYKDGTITTK
ELGTVMRSLGQNPTEAELQDMINEVDADGNGTIYFPEFLTMMARKMKDTDSEEIREAFRVFDKD
GNGYISAAQLRHVMTNLGEKLTDEEVDEMIREADIDGDGQVNYEEFVQMMTAKGGKRWKNFIA
VSAANRFKKISELMVSKGEELFTGVVPILVELDGDVNGHKFSVSGEGEGDATYGKLTLKFICTTG
KLPVPWPTLVTTLTGVQCFSRYPDHMKQHDFFKSAMPEGYVQERTIFFKDDGNYKTRAEVKFEG
DTLVNRIELKGIDFKEDGNILGHKLEYNYNSHNVYIMADKQKNGIKVNEKIRHNIEDGSVQLADH
YQQNTPIGDGPVLLPDNHYLSTQSALSKDPNEKRDHMVLLEFVTAAGITLGMDELYK*

*FIG. 9-3*

(SEQ ID. NO:7)
ATGCTGCTGCCCGTCCCCCTGCTGCTGGCCTGCTGGCGCCCGCCGCGACGTGAGCAAGGGCGA
GGAGCTGTTCACCGGGGTGGTGCCCATCCTGGTCGAGCTGGACGGCGACGTAAACGGCCACAAGT
TCAGCGTGTCCGGCGAGGGCGAGGGCGATGCCACCTACGGCAAGCTGACCCTGAAGTTCATCTGC
ACCACCGGCAAGCTGCCCGTGCCCTGGCCCACCCTCGTGACCACCCTGACCTACGGCGTGCAGTG
CTTCAGCCGCTACCCCGACCACATGAAGCAGCACGACTTCTTCAAGTCCGCCATGCCCGAAGGCT
ACGTCCAGGAGCGCACCATCTTCTTCAAGGACGACGGCAACTACAAGACCCGCGCCGAGGTGAAG
TTCGAGGGCGACACCCTGGTGAACCGCATCGAGCTGAAGGGCATCGACTTCAAGGAGGACGGCAA
CATCCTGGGGCACAAGCTGGAGTACAACTTCAACAGCCACAACGTCTATATCATGGCCGACAAGC
AGAAGAACGGCATCAAGGTGAACTTCAAGATCCGCCACAACATCGAGGACGGCAGCGTGCAGCTC
GCCGACCACTACCAGCAGAACACCCCCATCGGCGACGGCCCCGTGCTGCTGCCCGACAACCACTA
CCTGAGCACCCAGTCCGCCCTGAGCAAAGACCCCAACGAGAAGCGCGATCACATGGTCCTGCTGG
AGTTCGTGACCGCCGCCGGGATCACTCTCGGCATGGACGAGCTGTACAAGTAAAGCGGCCGCGAC
TCTAGATCATAATCAGCCATACCACATTTGTAGAGGTTTTACTTGCTTTAAAAAACCTCCCACA
CCTCCCCCTGAACCTGAAACATAAAATGAATGCAATTGTTGTTGTTAACTTGTTTATTGCAGCTT
ATAATGGTTACAAATAAAGCAATAGCATCACAAATTTCACAAATAAAGCATTTTTTTCACTGC
ATTCTAGTTGTGGTTTGTCCAAACTCATCAATGTATCTTAT
FIG. 10-1

(SEQ ID. NO:7)

AAATGATAAGGAAGCAGATATCGATGGTGATGGCCAAGTAAACTATGAAGAGTTTGTACAAATG
ATGACAGCAAGGGGGAAGAGCGCTGGAAGAAAACTTCATTGCCGTCAGCGCTGCCAACCG
GTTCAAGAAGATCTCCGAGCTCATGGTGAGCGAGAGCTGTTCACCGGGGTGGTGCCCA
TCCTGGTCGAGCTGGACGGCGAGGTAAACGGCCACAAGTTCAGCGTGTCCGGCGAGGGCGAGGGC
GATGCCACCTACGGCAAGCTGACCCTGAAGTTCATCTGCACCACCGGCAAGCTGCCCGTGCCCTG
GCCCACCCTCGTGACCACCCTGACCTACGGCGTGCAGTGCTTCAGCCGCTACCCCGACCACATGA
AGCAGCACGACTTCTTCAAGTCCGCCATGCCCGAAGGCTACGTCCAGGAGCGCACCATCTTCTTC
AAGGACGACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGGAGTACA
ACTACAACAGCCACAAGTCTATATCATGGCCGACAAGCAGAAGAACGGCATCAAGGTGAACTTC
AAGATCCGCCACAACATCGAGGACGGCAGCGTGCAGCTCGCCGACAACCACTACCTGAGCACCCC
CATCGGCGACGGCCCCGTGCTGCTGCCCGACAACCACTACCTGAGCACCCAGTCCGCCCTGAGCA
AAGACCCCAACGAGAAGCGCGATCACATGGTCCTGCTGGAGTTCGTGACCGCCGCCGGGATCACT
CTCGGGCAAGGAGGACGAGCTGTAA

FIG. 10-2

(SEQ ID. NO:8)
MLLPVPLLIGLLIGAAADVSKGEELFTGVVPILVELDGDVNGHKFSVSGEGEGDATYGKLTLKFIC
TTGKLPVPWPTLVTTLTHGVQCFSRYPDHMKQHDFFKSAMPEGYVQERTIFFKDGNYKTRAEVK
FEGDTLVNRIELKGIDFKEDGNILGHKLEYNENSHNVYIMADKQKNGIKVNFKIRHNIEDGSVQL
ADHYQQNTPIGDPVLLPDNHYLSTQSALSKDPNEKRDHMVLLEFVTAARMHDQLTEEQIAEFKE
AFSLFDKDGDGTITTKELGTVMRSLGQNPTEAELQDMINEVDADGNGTIYFPEFLTMMARKMDT
DSEEEIREAFRVFDKDGNGYISAAQLRHVMTNLGEKLTDEEVDEMIREADIDGDGQVNYEEFVQM
MTAKGGKRRWKKNFIAVSAANRFKKISELMVSKGEELFTGVVPILVELDGDVNGHKFSVSGEGEG
DATYGKLTLKFICTTGKLPVPWPTLVTTLTLYGVQCFSRYPDHMKQHDFFKSAMPEGYVQERTIFF
KDDGNYKTRAEVKFEGDTLVNRIELKGIDFKEDGNILGHKLEYNNSHNVYIMADKQKNGIKVNF
KIRHNIEDGSVQLADHYQQNTPIGDGPVLLPDNHYLSTQSALSKDPNEKRDHMVLLEFVTAAGIT
LGKDEL*

*FIG. 10-3*

SEQUENCE LISTING

<160> NUMBER OF SEQ ID NOS: 56

<210> SEQ ID NO 1
<211> LENGTH: 1929
<212> TYPE: DNA
<213> ORGANISM: Aequorea victoria
<220> FEATURE:
<221> NAME/KEY: CDS
<222> LOCATION: (0)...(1926)

<400> SEQUENCE: 1

```
atg gtg agc aag ggc gag gag ctg ttc acc ggg gtg gtg ccc atc ctg      48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
     50                  55                  60 ctg acc cat ggc gtg cag tgc ttc agc cgc tac ccc gac cac atg aag     240
Leu Thr His Gly Val Gln Cys Phe Ser Arg Tyr Pro Asp His Met Lys
 65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110
```

```
gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac      432
Ile Asp Phe Lys Glu Asp Gly Asn Ile Leu Gly His Lys Leu Glu Tyr
130                 135                 140 aac ttc aac agc cac aac gtc tat atc atg gcc gac aag cag aag aac      480
Asn Phe Asn Ser His Asn Val Tyr Ile Met Ala Asp Lys Gln Lys Asn
145                 150                 155                 160 ggc atc aag gtg aac ttc aag atc cgc cac aac atc gag gac ggc agc      528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc      576
Val Gln Leu Ala Asp His Tyr Gln Gln Asn Thr Pro Ile Gly Asp Gly
        180                 185                 190 ccc gtg ctg ctg ccc gac aac cac tac ctg agc acc cag tcc gcc ctg      624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
210                 215                 220 gtg acc gcc gcc cgc atg cat gac caa ctg aca gaa gag cag att gca      720
Val Thr Ala Ala Arg Met His Asp Gln Leu Thr Glu Glu Gln Ile Ala
225                 230                 235                 240 gag ttc aaa gaa gcc ttc tca tta ttc gac aag gat ggg gac ggc acc      768
Glu Phe Lys Glu Ala Phe Ser Leu Phe Asp Lys Asp Gly Asp Gly Thr
                245                 250                 255 atc acc aca aag gaa ctt ggc acc gtt atg agg tcg ctt gga caa aac      816
Ile Thr Thr Lys Glu Leu Gly Thr Val Met Arg Ser Leu Gly Gln Asn
        260                 265                 270 cca acg gaa gca gaa ttg cag gat atg atc aat gaa gtc gat gct gat      864
Pro Thr Glu Ala Glu Leu Gln Asp Met Ile Asn Glu Val Asp Ala Asp
        275                 280                 285 ggc aat gga acg att tac ttt cct gaa ttt ctt act atg atg gct aga      912
Gly Asn Gly Thr Ile Tyr Phe Pro Glu Phe Leu Thr Met Met Ala Arg
290                 295                 300 aaa atg aag gac aca gac agc gaa gag gaa atc cga gaa gca ttc cgt      960
Lys Met Lys Asp Thr Asp Ser Glu Glu Glu Ile Arg Glu Ala Phe Arg
305                 310                 315                 320 gtt ttt gac aag gat ggg aac ggc tac atc agc gct gct gaa tta cgt     1008
Val Phe Asp Lys Asp Gly Asn Gly Tyr Ile Ser Ala Ala Glu Leu Arg
                325                 330                 335 cac gtc atg aca aac ctc ggg gag aag tta aca gat gaa gaa gtt gat     1056
His Val Met Thr Asn Leu Gly Glu Lys Leu Thr Asp Glu Glu Val Asp
        340                 345                 350 gaa atg ata agg gaa gca gat atc gat ggt gat ggc caa gta aac tat     1104
Glu Met Ile Arg Glu Ala Asp Ile Asp Gly Asp Gly Gln Val Asn Tyr
        355                 360                 365 gaa gag ttt gta caa atg atg aca gca aag ggg ggg aag agg cgc tgg     1152
Glu Glu Phe Val Gln Met Met Thr Ala Lys Gly Gly Lys Arg Arg Trp
370                 375                 380 aag aaa aac ttc att gcc gtc agc gct gcc aac cgg ttc aag aag atc     1200
Lys Lys Asn Phe Ile Ala Val Ser Ala Ala Asn Arg Phe Lys Lys Ile
385                 390                 395                 400 tcc gag ctc atg gtg agc aag ggc gag gag ctg ttc acc ggg gtg gtg     1248
Ser Glu Leu Met Val Ser Lys Gly Glu Glu Leu Phe Thr Gly Val Val
                405                 410                 415 ccc atc ctg gtc gag ctg gac ggc gac gta aac ggc cac aag ttc agc     1296
Pro Ile Leu Val Glu Leu Asp Gly Asp Val Asn Gly His Lys Phe Ser
        420                 425                 430
```

| | | | | | | | | | | | | | | | |
|---|---|---|---|---|---|---|---|---|---|---|---|---|---|---|---|
| gtg | tcc | ggc | gag | ggc | gag | ggc | gat | gcc | acc | tac | ggc | aag | ctg | acc | ctg | 1344 |
| Val | Ser | Gly | Glu | Gly | Glu | Gly | Asp | Ala | Thr | Tyr | Gly | Lys | Leu | Thr | Leu |
| | | 435 | | | | | 440 | | | | | 445 | | | |

```
gtg tcc ggc gag ggc gag ggc gat gcc acc tac ggc aag ctg acc ctg   1344
Val Ser Gly Glu Gly Glu Gly Asp Ala Thr Tyr Gly Lys Leu Thr Leu
            435                 440                 445 aag ttc atc tgc acc acc ggc aag ctg ccc gtg ccc tgg ccc acc ctc   1392
Lys Phe Ile Cys Thr Thr Gly Lys Leu Pro Val Pro Trp Pro Thr Leu
450                 455                 460 gtg acc acc ctg acc tac ggc gtg cag tgc ttc agc cgc tac ccc gac   1440
Val Thr Thr Leu Thr Tyr Gly Val Gln Cys Phe Ser Arg Tyr Pro Asp
465                 470                 475                 480 cac atg aag cag cac gac ttc ttc aag tcc gcc atg ccc gaa ggc tac   1488
His Met Lys Gln His Asp Phe Phe Lys Ser Ala Met Pro Glu Gly Tyr
                485                 490                 495 gtc cag gag cgc acc atc ttc ttc aag gac gac ggc aac tac aag acc   1536
Val Gln Glu Arg Thr Ile Phe Phe Lys Asp Asp Gly Asn Tyr Lys Thr
            500                 505                 510 cgc gcc gag gtg aag ttc gag ggc gac acc ctg gtg aac cgc atc gag   1584
Arg Ala Glu Val Lys Phe Glu Gly Asp Thr Leu Val Asn Arg Ile Glu
        515                 520                 525 ctg aag ggc atc gac ttc aag gag gac ggc aac atc ctg ggg cac aag   1632
Leu Lys Gly Ile Asp Phe Lys Glu Asp Gly Asn Ile Leu Gly His Lys
    530                 535                 540 ctg gag tac aac tac aac agc cac aac gtc tat atc atg gcc gac aag   1680
Leu Glu Tyr Asn Tyr Asn Ser His Asn Val Tyr Ile Met Ala Asp Lys
545                 550                 555                 560 cag aag aac ggc atc aag gtg aac ttc aag atc cgc cac aac atc gag   1728
Gln Lys Asn Gly Ile Lys Val Asn Phe Lys Ile Arg His Asn Ile Glu
                565                 570                 575 gac ggc agc gtg cag ctc gcc gac cac tac cag cag aac acc ccc atc   1776
Asp Gly Ser Val Gln Leu Ala Asp His Tyr Gln Gln Asn Thr Pro Ile
            580                 585                 590 ggc gac ggc ccc gtg ctg ctg ccc gac aac cac tac ctg agc acc cag   1824
Gly Asp Gly Pro Val Leu Leu Pro Asp Asn His Tyr Leu Ser Thr Gln
        595                 600                 605 tcc gcc ctg agc aaa gac ccc aac gag aag cgc gat cac atg gtc ctg   1872
Ser Ala Leu Ser Lys Asp Pro Asn Glu Lys Arg Asp His Met Val Leu
    610                 615                 620 ctg gag ttc gtg acc gcc gcc ggg atc act ctc ggc atg gac gag ctg   1920
Leu Glu Phe Val Thr Ala Ala Gly Ile Thr Leu Gly Met Asp Glu Leu
625                 630                 635                 640 tac aag taa                                                       1929
Tyr Lys
```

<210> SEQ ID NO 2
<211> LENGTH: 642
<212> TYPE: PRT
<213> ORGANISM: Aequorea victoria

<400> SEQUENCE: 2

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

-continued

Arg Thr Ile Phe Phe Lys Asp Asp Gly Asn Tyr Lys Thr Arg Ala Glu
                100                 105                 110
Val Lys Phe Glu Gly Asp Thr Leu Val Asn Arg Ile Glu Leu Lys Gly
            115                 120                 125
Ile Asp Phe Lys Glu Asp Gly Asn Ile Leu Gly His Lys Leu Glu Tyr
        130                 135                 140
Asn Phe Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
210                 215                 220
Val Thr Ala Ala Arg Met His Asp Gln Leu Thr Glu Glu Gln Ile Ala
225                 230                 235                 240
Glu Phe Lys Glu Ala Phe Ser Leu Phe Asp Lys Asp Gly Asp Gly Thr
                245                 250                 255
Ile Thr Thr Lys Glu Leu Gly Thr Val Met Arg Ser Leu Gly Gln Asn
            260                 265                 270
Pro Thr Glu Ala Glu Leu Gln Asp Met Ile Asn Glu Val Asp Ala Asp
        275                 280                 285
Gly Asn Gly Thr Ile Tyr Phe Pro Glu Phe Leu Thr Met Met Ala Arg
290                 295                 300
Lys Met Lys Asp Thr Asp Ser Glu Glu Glu Ile Arg Glu Ala Phe Arg
305                 310                 315                 320
Val Phe Asp Lys Asp Gly Asn Gly Tyr Ile Ser Ala Ala Glu Leu Arg
                325                 330                 335
His Val Met Thr Asn Leu Gly Glu Lys Leu Thr Asp Glu Glu Val Asp
            340                 345                 350
Glu Met Ile Arg Glu Ala Asp Ile Asp Gly Asp Gly Gln Val Asn Tyr
        355                 360                 365
Glu Glu Phe Val Gln Met Met Thr Ala Lys Gly Gly Lys Arg Arg Trp
370                 375                 380
Lys Lys Asn Phe Ile Ala Val Ser Ala Ala Asn Arg Phe Lys Lys Ile
385                 390                 395                 400
Ser Glu Leu Met Val Ser Lys Gly Glu Glu Leu Phe Thr Gly Val Val
                405                 410                 415
Pro Ile Leu Val Glu Leu Asp Gly Asp Val Asn Gly His Lys Phe Ser
            420                 425                 430
Val Ser Gly Glu Gly Glu Gly Asp Ala Thr Tyr Gly Lys Leu Thr Leu
        435                 440                 445
Lys Phe Ile Cys Thr Thr Gly Lys Leu Pro Val Pro Trp Pro Thr Leu
        450                 455                 460
Val Thr Thr Leu Thr Tyr Gly Val Gln Cys Phe Ser Arg Tyr Pro Asp
465                 470                 475                 480
His Met Lys Gln His Asp Phe Phe Lys Ser Ala Met Pro Glu Gly Tyr
                485                 490                 495
Val Gln Glu Arg Thr Ile Phe Phe Lys Asp Asp Gly Asn Tyr Lys Thr
            500                 505                 510
Arg Ala Glu Val Lys Phe Glu Gly Asp Thr Leu Val Asn Arg Ile Glu
        515                 520                 525

-continued

```
Leu Lys Gly Ile Asp Phe Lys Glu Asp Gly Asn Ile Leu Gly His Lys
        530                 535                 540
Leu Glu Tyr Asn Tyr Asn Ser His Asn Val Tyr Ile Met Ala Asp Lys
545                 550                 555                 560
Gln Lys Asn Gly Ile Lys Val Asn Phe Lys Ile Arg His Asn Ile Glu
                565                 570                 575
Asp Gly Ser Val Gln Leu Ala Asp His Tyr Gln Gln Asn Thr Pro Ile
            580                 585                 590
Gly Asp Gly Pro Val Leu Leu Pro Asp Asn His Tyr Leu Ser Thr Gln
        595                 600                 605
Ser Ala Leu Ser Lys Asp Pro Asn Glu Lys Arg Asp His Met Val Leu
    610                 615                 620
Leu Glu Phe Val Thr Ala Ala Gly Ile Thr Leu Gly Met Asp Glu Leu
625                 630                 635                 640
Tyr Lys
```

<210> SEQ ID NO 3
<211> LENGTH: 1959
<212> TYPE: DNA
<213> ORGANISM: Aequorea victoria
<220> FEATURE:
<221> NAME/KEY: CDS
<222> LOCATION: (0)...(1956)

<400> SEQUENCE: 3

```
atg gtg agc aag ggc gag gag ctg ttc acc ggg gtg gtg ccc atc ctg     48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc     96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc    144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc    192
Cys Thr Thr Gly Lys Leu Pro Val Pro Trp Pro Thr Leu Val Thr Thr
    50                  55                  60 ctg acc cat ggc gtg cag tgc ttc agc cgc tac ccc gac cac atg aag    240
Leu Thr His Gly Val Gln Cys Phe Ser Arg Tyr Pro Asp His Met Lys
65                  70                  75                  80 cag cac gac ttc ttc aag tcc gcc atg ccc gaa ggc tac gtc cag gag    288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag    336
Arg Thr Ile Phe Phe Lys Asp Asp Gly Asn Tyr Lys Thr Arg Ala Glu
           100                 105                 110 gtg aag ttc gag ggc gac acc ctg gtg aac cgc atc gag ctg aag ggc    384
Val Lys Phe Glu Gly Asp Thr Leu Val Asn Arg Ile Glu Leu Lys Gly
       115                 120                 125 atc gac ttc aag gag gac ggc aac atc ctg ggg cac aag ctg gag tac    432
Ile Asp Phe Lys Glu Asp Gly Asn Ile Leu Gly His Lys Leu Glu Tyr
   130                 135                 140 aac ttc aac agc cac aac gtc tat atc atg gcc gac aag cag aag aac    480
Asn Phe Asn Ser His Asn Val Tyr Ile Met Ala Asp Lys Gln Lys Asn
145                 150                 155                 160 ggc atc aag gtg aac ttc aag atc cgc cac aac atc gag gac ggc agc    528
Gly Ile Lys Val Asn Phe Lys Ile Arg His Asn Ile Glu Asp Gly Ser
                165                 170                 175
```

```
gtg cag ctc gcc gac cac tac cag cag aac acc ccc atc ggc gac ggc    576
Val Gln Leu Ala Asp His Tyr Gln Gln Asn Thr Pro Ile Gly Asp Gly
        180                 185                 190 ccc gtg ctg ctg ccc gac aac cac tac ctg agc acc cag tcc gcc ctg    624
Pro Val Leu Leu Pro Asp Asn His Tyr Leu Ser Thr Gln Ser Ala Leu
    195                 200                 205 agc aaa gac ccc aac gag aag cgc gat cac atg gtc ctg ctg gag ttc    672
Ser Lys Asp Pro Asn Glu Lys Arg Asp His Met Val Leu Leu Glu Phe
210                 215                 220 gtg acc gcc gcc cgc atg cat gac caa ctg aca gaa gag cag att gca    720
Val Thr Ala Ala Arg Met His Asp Gln Leu Thr Glu Glu Gln Ile Ala
225                 230                 235                 240 gag ttc aaa gaa gcc ttc tca tta ttc gac aag gat ggg gac ggc acc    768
Glu Phe Lys Glu Ala Phe Ser Leu Phe Asp Lys Asp Gly Asp Gly Thr
                245                 250                 255 atc acc aca aag gaa ctt ggc acc gtt atg agg tcg ctt gga caa aac    816
Ile Thr Thr Lys Glu Leu Gly Thr Val Met Arg Ser Leu Gly Gln Asn
            260                 265                 270 cca acg gaa gca gaa ttg cag gat atg atc aat gaa gtc gat gct gat    864
Pro Thr Glu Ala Glu Leu Gln Asp Met Ile Asn Glu Val Asp Ala Asp
        275                 280                 285 ggc aat gga acg att tac ttt cct gaa ttt ctt act atg atg gct aga    912
Gly Asn Gly Thr Ile Tyr Phe Pro Glu Phe Leu Thr Met Met Ala Arg
    290                 295                 300 aaa atg aag gac aca gac agc gaa gag gaa atc cga gaa gca ttc cgt    960
Lys Met Lys Asp Thr Asp Ser Glu Glu Glu Ile Arg Glu Ala Phe Arg
305                 310                 315                 320 gtt ttt gac aag gat ggg aac ggc tac atc agc gct gct gaa tta cgt   1008
Val Phe Asp Lys Asp Gly Asn Gly Tyr Ile Ser Ala Ala Glu Leu Arg
                325                 330                 335 cac gtc atg aca aac ctc ggg gag aag tta aca gat gaa gaa gtt gat   1056
His Val Met Thr Asn Leu Gly Glu Lys Leu Thr Asp Glu Glu Val Asp
            340                 345                 350 gaa atg ata agg gaa gca gat atc gat ggt gat ggc caa gta aac tat   1104
Glu Met Ile Arg Glu Ala Asp Ile Asp Gly Asp Gly Gln Val Asn Tyr
        355                 360                 365 gaa gag ttt gta caa atg atg aca gca aag ggg ggg aag agg cgc tgg   1152
Glu Glu Phe Val Gln Met Met Thr Ala Lys Gly Gly Lys Arg Arg Trp
    370                 375                 380 aag aaa aac ttc att gcc gtc agc gct gcc aac cgg ttc aag aag atc   1200
Lys Lys Asn Phe Ile Ala Val Ser Ala Ala Asn Arg Phe Lys Lys Ile
385                 390                 395                 400 tcc gag ctc atg gtg agc aag ggc gag gag ctg ttc acc ggg gtg gtg   1248
Ser Glu Leu Met Val Ser Lys Gly Glu Glu Leu Phe Thr Gly Val Val
                405                 410                 415 ccc atc ctg gtc gag ctg gac ggc gac gta aac ggc cac aag ttc agc   1296
Pro Ile Leu Val Glu Leu Asp Gly Asp Val Asn Gly His Lys Phe Ser
            420                 425                 430 gtg tcc ggc gag ggc gag ggc gat gcc acc tac ggc aag ctg acc ctg   1344
Val Ser Gly Glu Gly Glu Gly Asp Ala Thr Tyr Gly Lys Leu Thr Leu
        435                 440                 445 aag ttc atc tgc acc acc ggc aag ctg ccc gtg ccc tgg ccc acc ctc   1392
Lys Phe Ile Cys Thr Thr Gly Lys Leu Pro Val Pro Trp Pro Thr Leu
    450                 455                 460 gtg acc acc ctg acc tac ggc gtg cag tgc ttc agc cgc tac ccc gac   1440
Val Thr Thr Leu Thr Tyr Gly Val Gln Cys Phe Ser Arg Tyr Pro Asp
465                 470                 475                 480 cac atg aag cag cac gac ttc ttc aag tcc gcc atg ccc gaa ggc tac   1488
His Met Lys Gln His Asp Phe Phe Lys Ser Ala Met Pro Glu Gly Tyr
                485                 490                 495
```

-continued

| | | | | | | | | | | | | | | | | |
|---|---|---|---|---|---|---|---|---|---|---|---|---|---|---|---|---|
| gtc | cag | gag | cgc | acc | atc | ttc | ttc | aag | gac | gac | ggc | aac | tac | aag | acc | 1536 |
| Val | Gln | Glu | Arg | Thr | Ile | Phe | Phe | Lys | Asp | Asp | Gly | Asn | Tyr | Lys | Thr | |
| | | 500 | | | | | 505 | | | | | 510 | | | | |

| cgc | gcc | gag | gtg | aag | ttc | gag | ggc | gac | acc | ctg | gtg | aac | cgc | atc | gag | 1584 |
| Arg | Ala | Glu | Val | Lys | Phe | Glu | Gly | Asp | Thr | Leu | Val | Asn | Arg | Ile | Glu | |
| | 515 | | | | | 520 | | | | | 525 | | | | | |

| ctg | aag | ggc | atc | gac | ttc | aag | gag | gac | ggc | aac | atc | ctg | ggg | cac | aag | 1632 |
| Leu | Lys | Gly | Ile | Asp | Phe | Lys | Glu | Asp | Gly | Asn | Ile | Leu | Gly | His | Lys | |
| 530 | | | | | 535 | | | | | 540 | | | | | | |

| ctg | gag | tac | aac | tac | aac | agc | cac | aac | gtc | tat | atc | atg | gcc | gac | aag | 1680 |
| Leu | Glu | Tyr | Asn | Tyr | Asn | Ser | His | Asn | Val | Tyr | Ile | Met | Ala | Asp | Lys | |
| 545 | | | | 550 | | | | | 555 | | | | | 560 | | |

| cag | aag | aac | ggc | atc | aag | gtg | aac | ttc | aag | atc | cgc | cac | aac | atc | gag | 1728 |
| Gln | Lys | Asn | Gly | Ile | Lys | Val | Asn | Phe | Lys | Ile | Arg | His | Asn | Ile | Glu | |
| | | | 565 | | | | | 570 | | | | | 575 | | | |

| gac | ggc | agc | gtg | cag | ctc | gcc | gac | cac | tac | cag | cag | aac | acc | ccc | atc | 1776 |
| Asp | Gly | Ser | Val | Gln | Leu | Ala | Asp | His | Tyr | Gln | Gln | Asn | Thr | Pro | Ile | |
| | | 580 | | | | | 585 | | | | | 590 | | | | |

| ggc | gac | ggc | ccc | gtg | ctg | ctg | ccc | gac | aac | cac | tac | ctg | agc | acc | cag | 1824 |
| Gly | Asp | Gly | Pro | Val | Leu | Leu | Pro | Asp | Asn | His | Tyr | Leu | Ser | Thr | Gln | |
| | 595 | | | | | 600 | | | | | 605 | | | | | |

| tcc | gcc | ctg | agc | aaa | gac | ccc | aac | gag | aag | cgc | gat | cac | atg | gtc | ctg | 1872 |
| Ser | Ala | Leu | Ser | Lys | Asp | Pro | Asn | Glu | Lys | Arg | Asp | His | Met | Val | Leu | |
| 610 | | | | | 615 | | | | | 620 | | | | | | |

| ctg | gag | ttc | gtg | acc | gcc | gcc | ggg | atc | act | ctc | ggc | atg | gac | gag | ctg | 1920 |
| Leu | Glu | Phe | Val | Thr | Ala | Ala | Gly | Ile | Thr | Leu | Gly | Met | Asp | Glu | Leu | |
| 625 | | | | 630 | | | | | 635 | | | | | 640 | | |

| tac | aag | cca | aaa | aag | aag | aga | aag | gtg | gaa | gac | gct | taa | | | | 1959 |
| Tyr | Lys | Pro | Lys | Lys | Lys | Arg | Lys | Val | Glu | Asp | Ala | | | | | |
| | | | | 645 | | | | | 650 | | | | | | | |

<210> SEQ ID NO 4
<211> LENGTH: 652
<212> TYPE: PRT
<213> ORGANISM: Aequorea victoria

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Leu Val Thr Thr
        50                  55                  60

Leu Thr His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

```
Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Arg Met His Asp Gln Leu Thr Glu Glu Gln Ile Ala
225                 230                 235                 240

Glu Phe Lys Glu Ala Phe Ser Leu Phe Asp Lys Asp Gly Asp Gly Thr
                245                 250                 255

Ile Thr Thr Lys Glu Leu Gly Thr Val Met Arg Ser Leu Gly Gln Asn
        260                 265                 270

Pro Thr Glu Ala Glu Leu Gln Asp Met Ile Asn Glu Val Asp Ala Asp
        275                 280                 285

Gly Asn Gly Thr Ile Tyr Phe Pro Glu Phe Leu Thr Met Met Ala Arg
        290                 295                 300

Lys Met Lys Asp Thr Asp Ser Glu Glu Glu Ile Arg Glu Ala Phe Arg
305                 310                 315                 320

Val Phe Asp Lys Asp Gly Asn Gly Tyr Ile Ser Ala Ala Glu Leu Arg
                325                 330                 335

His Val Met Thr Asn Leu Gly Glu Lys Leu Thr Asp Glu Glu Val Asp
                340                 345                 350

Glu Met Ile Arg Glu Ala Asp Ile Asp Gly Asp Gly Gln Val Asn Tyr
            355                 360                 365

Glu Glu Phe Val Gln Met Met Thr Ala Lys Gly Gly Lys Arg Arg Trp
370                 375                 380

Lys Lys Asn Phe Ile Ala Val Ser Ala Ala Asn Arg Phe Lys Lys Ile
385                 390                 395                 400

Ser Glu Leu Met Val Ser Lys Gly Glu Glu Leu Phe Thr Gly Val Val
                405                 410                 415

Pro Ile Leu Val Glu Leu Asp Gly Asp Val Asn Gly His Lys Phe Ser
            420                 425                 430

Val Ser Gly Glu Gly Glu Gly Asp Ala Thr Tyr Gly Lys Leu Thr Leu
            435                 440                 445

Lys Phe Ile Cys Thr Thr Gly Lys Leu Pro Val Pro Trp Pro Thr Leu
        450                 455                 460

Val Thr Thr Leu Thr Tyr Gly Val Gln Cys Phe Ser Arg Tyr Pro Asp
465                 470                 475                 480

His Met Lys Gln His Asp Phe Phe Lys Ser Ala Met Pro Glu Gly Tyr
                485                 490                 495

Val Gln Glu Arg Thr Ile Phe Phe Lys Asp Asp Gly Asn Tyr Lys Thr
            500                 505                 510

Arg Ala Glu Val Lys Phe Glu Gly Asp Thr Leu Val Asn Arg Ile Glu
            515                 520                 525

Leu Lys Gly Ile Asp Phe Lys Glu Asp Gly Asn Ile Leu Gly His Lys
        530                 535                 540

Leu Glu Tyr Asn Tyr Asn Ser His Asn Val Tyr Ile Met Ala Asp Lys
545                 550                 555                 560

Gln Lys Asn Gly Ile Lys Val Asn Phe Lys Ile Arg His Asn Ile Glu
                565                 570                 575

Asp Gly Ser Val Gln Leu Ala Asp His Tyr Gln Gln Asn Thr Pro Ile
            580                 585                 590

Gly Asp Gly Pro Val Leu Leu Pro Asp Asn His Tyr Leu Ser Thr Gln
        595                 600                 605
```

```
Ser Ala Leu Ser Lys Asp Pro Asn Glu Lys Arg Asp His Met Val Leu
    610             615                 620

Leu Glu Phe Val Thr Ala Ala Gly Ile Thr Leu Gly Met Asp Glu Leu
625             630                 635                 640

Tyr Lys Pro Lys Lys Lys Arg Lys Val Glu Asp Ala
                645                 650
```

<210> SEQ ID NO 5
<211> LENGTH: 1929
<212> TYPE: DNA
<213> ORGANISM: Aequorea victoria
<220> FEATURE:
<221> NAME/KEY: CDS
<222> LOCATION: (0)...(1926)

<400> SEQUENCE: 5

```
atg gtg agc aag ggc gag gag ctg ttc acc ggg gtg gtg ccc atc ctg    48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc    96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc   144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc   192
Cys Thr Thr Gly Lys Leu Pro Val Pro Trp Pro Thr Leu Val Thr Thr
    50                  55                  60 ctg acc cat ggc gtg cag tgc ttc agc cgc tac ccc gac cac atg aag   240
Leu Thr His Gly Val Gln Cys Phe Ser Arg Tyr Pro Asp His Met Lys
65                  70                  75                  80 cag cac gac ttc ttc aag tcc gcc atg ccc gaa ggc tac gtc cag gag   288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag   336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc   384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac   432
Ile Asp Phe Lys Glu Asp Gly Asn Ile Leu Gly His Lys Leu Glu Tyr
    130                 135                 140 aac ttc aac agc cac aac gtc tat atc atg gcc gac aag cag aag aac   480
Asn Phe Asn Ser His Asn Val Tyr Ile Met Ala Asp Lys Gln Lys Asn
145                 150                 155                 160 ggc atc aag gtg aac ttc aag atc cgc cac aac atc gag gac ggc agc   528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc   576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg   624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc   672
Ser Lys Asp Pro Asn Glu Lys Arg Asp His Met Val Leu Leu Glu Phe
    210                 215                 220 gtg acc gcc gcc cgc atg cat gac caa ctg aca gaa gag cag att gca   720
Val Thr Ala Ala Arg Met His Asp Gln Leu Thr Glu Glu Gln Ile Ala
225                 230                 235                 240
```

```
gag ttc aaa gaa gcc ttc tca tta ttc gac aag gat ggg gac ggc acc      768
Glu Phe Lys Glu Ala Phe Ser Leu Phe Asp Lys Asp Gly Asp Gly Thr
                245                 250                 255 atc acc aca aag gaa ctt ggc acc gtt atg agg tcg ctt gga caa aac      816
Ile Thr Thr Lys Glu Leu Gly Thr Val Met Arg Ser Leu Gly Gln Asn
                260                 265                 270 cca acg gaa gca gaa ttg cag gat atg atc aat gaa gtc gat gct gat      864
Pro Thr Glu Ala Glu Leu Gln Asp Met Ile Asn Glu Val Asp Ala Asp
            275                 280                 285 ggc aat gga acg att tac ttt cct gaa ttt ctt act atg atg gct aga      912
Gly Asn Gly Thr Ile Tyr Phe Pro Glu Phe Leu Thr Met Met Ala Arg
        290                 295                 300 aaa atg aag gac aca gac agc gaa gag gaa atc cga gaa gca ttc cgt      960
Lys Met Lys Asp Thr Asp Ser Glu Glu Glu Ile Arg Glu Ala Phe Arg
305                 310                 315                 320 gtt ttt gac aag gat ggg aac ggc tac atc agc gct gct cag tta cgt     1008
Val Phe Asp Lys Asp Gly Asn Gly Tyr Ile Ser Ala Ala Gln Leu Arg
                325                 330                 335 cac gtc atg aca aac ctc ggg gag aag tta aca gat gaa gaa gtt gat     1056
His Val Met Thr Asn Leu Gly Glu Lys Leu Thr Asp Glu Glu Val Asp
                340                 345                 350 gaa atg ata agg gaa gca gat atc gat ggt gat ggc caa gta aac tat     1104
Glu Met Ile Arg Glu Ala Asp Ile Asp Gly Asp Gly Gln Val Asn Tyr
            355                 360                 365 gaa gag ttt gta caa atg atg aca gca aag ggg ggg aag agg cgc tgg     1152
Glu Glu Phe Val Gln Met Met Thr Ala Lys Gly Gly Lys Arg Arg Trp
        370                 375                 380 aag aaa aac ttc att gcc gtc agc gct gcc aac cgg ttc aag aag atc     1200
Lys Lys Asn Phe Ile Ala Val Ser Ala Ala Asn Arg Phe Lys Lys Ile
385                 390                 395                 400 tcc gag ctc atg gtg agc aag ggc gag gag ctg ttc acc ggg gtg gtg     1248
Ser Glu Leu Met Val Ser Lys Gly Glu Glu Leu Phe Thr Gly Val Val
                405                 410                 415 ccc atc ctg gtc gag ctg gac ggc gac gta aac ggc cac aag ttc agc     1296
Pro Ile Leu Val Glu Leu Asp Gly Asp Val Asn Gly His Lys Phe Ser
                420                 425                 430 gtg tcc ggc gag ggc gag ggc gat gcc acc tac ggc aag ctg acc ctg     1344
Val Ser Gly Glu Gly Glu Gly Asp Ala Thr Tyr Gly Lys Leu Thr Leu
            435                 440                 445 aag ttc atc tgc acc acc ggc aag ctg ccc gtg ccc tgg ccc acc ctc     1392
Lys Phe Ile Cys Thr Thr Gly Lys Leu Pro Val Pro Trp Pro Thr Leu
        450                 455                 460 gtg acc acc ctg acc tac ggc gtg cag tgc ttc agc cgc tac ccc gac     1440
Val Thr Thr Leu Thr Tyr Gly Val Gln Cys Phe Ser Arg Tyr Pro Asp
465                 470                 475                 480 cac atg aag cag cac gac ttc ttc aag tcc gcc atg ccc gaa ggc tac     1488
His Met Lys Gln His Asp Phe Phe Lys Ser Ala Met Pro Glu Gly Tyr
                485                 490                 495 gtc cag gag cgc acc atc ttc ttc aag gac gac ggc aac tac aag acc     1536
Val Gln Glu Arg Thr Ile Phe Phe Lys Asp Asp Gly Asn Tyr Lys Thr
                500                 505                 510 cgc gcc gag gtg aag ttc gag ggc gac acc ctg gtg aac cgc atc gag     1584
Arg Ala Glu Val Lys Phe Glu Gly Asp Thr Leu Val Asn Arg Ile Glu
            515                 520                 525 ctg aag ggc atc gac ttc aag gag gac ggc aac atc ctg ggg cac aag     1632
Leu Lys Gly Ile Asp Phe Lys Glu Asp Gly Asn Ile Leu Gly His Lys
        530                 535                 540 ctg gag tac aac tac aac agc cac aac gtc tat atc atg gcc gac aag     1680
Leu Glu Tyr Asn Tyr Asn Ser His Asn Val Tyr Ile Met Ala Asp Lys
545                 550                 555                 560
```

```
cag aag aac ggc atc aag gtg aac ttc aag atc cgc cac aac atc gag    1728
Gln Lys Asn Gly Ile Lys Val Asn Phe Lys Ile Arg His Asn Ile Glu
            565                 570                 575 gac ggc agc gtg cag ctc gcc gac cac tac cag cag aac acc ccc atc    1776
Asp Gly Ser Val Gln Leu Ala Asp His Tyr Gln Gln Asn Thr Pro Ile
        580                 585                 590 ggc gac ggc ccc gtg ctg ctg ccc gac aac cac tac ctg agc acc cag    1824
Gly Asp Gly Pro Val Leu Leu Pro Asp Asn His Tyr Leu Ser Thr Gln
        595                 600                 605 tcc gcc ctg agc aaa gac ccc aac gag aag cgc gat cac atg gtc ctg    1872
Ser Ala Leu Ser Lys Asp Pro Asn Glu Lys Arg Asp His Met Val Leu
        610                 615                 620 ctg gag ttc gtg acc gcc gcc ggg atc act ctc ggc atg gac gag ctg    1920
Leu Glu Phe Val Thr Ala Ala Gly Ile Thr Leu Gly Met Asp Glu Leu
625                 630                 635                 640 tac aag taa                                                         1929
Tyr Lys
```

<210> SEQ ID NO 6
<211> LENGTH: 642
<212> TYPE: PRT
<213> ORGANISM: Aequorea victoria

<400> SEQUENCE: 6

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Arg Met His Asp Gln Leu Thr Glu Glu Gln Ile Ala
225                 230                 235                 240

Glu Phe Lys Glu Ala Phe Ser Leu Phe Asp Lys Asp Gly Asp Gly Thr
                245                 250                 255
```

Ile Thr Thr Lys Glu Leu Gly Thr Val Met Arg Ser Leu Gly Gln Asn
        260                 265                 270

Pro Thr Glu Ala Glu Leu Gln Asp Met Ile Asn Glu Val Asp Ala Asp
            275                 280                 285

Gly Asn Gly Thr Ile Tyr Phe Pro Glu Phe Leu Thr Met Met Ala Arg
290                 295                 300

Lys Met Lys Asp Thr Asp Ser Glu Glu Ile Arg Glu Ala Phe Arg
305                 310                 315                 320

Val Phe Asp Lys Asp Gly Asn Gly Tyr Ile Ser Ala Ala Gln Leu Arg
                325                 330                 335

His Val Met Thr Asn Leu Gly Glu Lys Leu Thr Asp Glu Glu Val Asp
            340                 345                 350

Glu Met Ile Arg Glu Ala Asp Ile Asp Gly Asp Gly Gln Val Asn Tyr
        355                 360                 365

Glu Glu Phe Val Gln Met Met Thr Ala Lys Gly Gly Lys Arg Arg Trp
370                 375                 380

Lys Lys Asn Phe Ile Ala Val Ser Ala Ala Asn Arg Phe Lys Lys Ile
385                 390                 395                 400

Ser Glu Leu Met Val Ser Lys Gly Glu Glu Leu Phe Thr Gly Val Val
                405                 410                 415

Pro Ile Leu Val Glu Leu Asp Gly Asp Val Asn Gly His Lys Phe Ser
            420                 425                 430

Val Ser Gly Glu Gly Glu Gly Asp Ala Thr Tyr Gly Lys Leu Thr Leu
        435                 440                 445

Lys Phe Ile Cys Thr Thr Gly Lys Leu Pro Val Pro Trp Pro Thr Leu
450                 455                 460

Val Thr Thr Leu Thr Tyr Gly Val Gln Cys Phe Ser Arg Tyr Pro Asp
465                 470                 475                 480

His Met Lys Gln His Asp Phe Phe Lys Ser Ala Met Pro Glu Gly Tyr
                485                 490                 495

Val Gln Glu Arg Thr Ile Phe Phe Lys Asp Asp Gly Asn Tyr Lys Thr
            500                 505                 510

Arg Ala Glu Val Lys Phe Glu Gly Asp Thr Leu Val Asn Arg Ile Glu
        515                 520                 525

Leu Lys Gly Ile Asp Phe Lys Glu Asp Gly Asn Ile Leu Gly His Lys
530                 535                 540

Leu Glu Tyr Asn Tyr Asn Ser His Asn Val Tyr Ile Met Ala Asp Lys
545                 550                 555                 560

Gln Lys Asn Gly Ile Lys Val Asn Phe Lys Ile Arg His Asn Ile Glu
                565                 570                 575

Asp Gly Ser Val Gln Leu Ala Asp His Tyr Gln Gln Asn Thr Pro Ile
            580                 585                 590

Gly Asp Gly Pro Val Leu Leu Pro Asp Asn His Tyr Leu Ser Thr Gln
        595                 600                 605

Ser Ala Leu Ser Lys Asp Pro Asn Glu Lys Arg Asp His Met Val Leu
610                 615                 620

Leu Glu Phe Val Thr Ala Ala Gly Ile Thr Leu Gly Met Asp Glu Leu
625                 630                 635                 640

Tyr Lys

<210> SEQ ID NO 7
<211> LENGTH: 1971
<212> TYPE: DNA
<213> ORGANISM: Aequorea victoria

```
<220> FEATURE:
<221> NAME/KEY: CDS
<222> LOCATION: (0)...(1968)

<400> SEQUENCE: 7 atg ctg ctg ccc gtc ccc ctg ctg ctg ggc ctg ctg ggc gcc gcc gcc        48
Met Leu Leu Pro Val Pro Leu Leu Leu Gly Leu Leu Gly Ala Ala Ala
 1               5                  10                  15 gac gtg agc aag ggc gag gag ctg ttc acc ggg gtg gtg ccc atc ctg        96
Asp Val Ser Lys Gly Glu Glu Leu Phe Thr Gly Val Val Pro Ile Leu
             20                  25                  30 gtc gag ctg gac ggc gac gta aac ggc cac aag ttc agc gtg tcc ggc       144
Val Glu Leu Asp Gly Asp Val Asn Gly His Lys Phe Ser Val Ser Gly
         35                  40                  45 gag ggc gag ggc gat gcc acc tac ggc aag ctg acc ctg aag ttc atc       192
Glu Gly Glu Gly Asp Ala Thr Tyr Gly Lys Leu Thr Leu Lys Phe Ile
     50                  55                  60 tgc acc acc ggc aag ctg ccc gtg ccc tgg ccc acc ctc gtg acc acc       240
Cys Thr Thr Gly Lys Leu Pro Val Pro Trp Pro Thr Leu Val Thr Thr
 65                  70                  75                  80 ctg acc cat ggc gtg cag tgc ttc agc cgc tac ccc gac cac atg aag       288
Leu Thr His Gly Val Gln Cys Phe Ser Arg Tyr Pro Asp His Met Lys
                 85                  90                  95 cag cac gac ttc ttc aag tcc gcc atg ccc gaa ggc tac gtc cag gag       336
Gln His Asp Phe Phe Lys Ser Ala Met Pro Glu Gly Tyr Val Gln Glu
            100                 105                 110 cgc acc atc ttc ttc aag gac gac ggc aac tac aag acc cgc gcc gag       384
Arg Thr Ile Phe Phe Lys Asp Asp Gly Asn Tyr Lys Thr Arg Ala Glu
        115                 120                 125 gtg aag ttc gag ggc gac acc ctg gtg aac cgc atc gag ctg aag ggc       432
Val Lys Phe Glu Gly Asp Thr Leu Val Asn Arg Ile Glu Leu Lys Gly
    130                 135                 140 atc gac ttc aag gag gac ggc aac atc ctg ggg cac aag ctg gag tac       480
Ile Asp Phe Lys Glu Asp Gly Asn Ile Leu Gly His Lys Leu Glu Tyr
145                 150                 155                 160 aac ttc aac agc cac aac gtc tat atc atg gcc gac aag cag aag aac       528
Asn Phe Asn Ser His Asn Val Tyr Ile Met Ala Asp Lys Gln Lys Asn
                165                 170                 175 ggc atc aag gtg aac ttc aag atc cgc cac aac atc gag gac ggc agc       576
Gly Ile Lys Val Asn Phe Lys Ile Arg His Asn Ile Glu Asp Gly Ser
            180                 185                 190 gtg cag ctc gcc gac cac tac cag cag aac acc ccc atc ggc gac ggc       624
Val Gln Leu Ala Asp His Tyr Gln Gln Asn Thr Pro Ile Gly Asp Gly
        195                 200                 205 ccc gtg ctg ctg ccc gac aac cac tac ctg agc acc cag tcc gcc ctg       672
Pro Val Leu Leu Pro Asp Asn His Tyr Leu Ser Thr Gln Ser Ala Leu
    210                 215                 220 agc aaa gac ccc aac gag aag cgc gat cac atg gtc ctg ctg gag ttc       720
Ser Lys Asp Pro Asn Glu Lys Arg Asp His Met Val Leu Leu Glu Phe
225                 230                 235                 240 gtg acc gcc gcc cgc atg cat gac caa ctg aca gaa gag cag att gca       768
Val Thr Ala Ala Arg Met His Asp Gln Leu Thr Glu Glu Gln Ile Ala
                245                 250                 255 gag ttc aaa gaa gcc ttc tca tta ttc gac aag gat ggg gac ggc acc       816
Glu Phe Lys Glu Ala Phe Ser Leu Phe Asp Lys Asp Gly Asp Gly Thr
            260                 265                 270 atc acc aca aag gaa ctt ggc acc gtt atg agg tcg ctt gga caa aac       864
Ile Thr Thr Lys Glu Leu Gly Thr Val Met Arg Ser Leu Gly Gln Asn
        275                 280                 285
```

| | |
|---|---|
| cca acg gaa gca gaa ttg cag gat atg atc aat gaa gtc gat gct gat<br>Pro Thr Glu Ala Glu Leu Gln Asp Met Ile Asn Glu Val Asp Ala Asp<br>290                                    295                              300 | 912 |
| ggc aat gga acg att tac ttt cct gaa ttt ctt act atg atg gct aga<br>Gly Asn Gly Thr Ile Tyr Phe Pro Glu Phe Leu Thr Met Met Ala Arg<br>305                                  310                              315                     320 | 960 |
| aaa atg aag gac aca gac agc gaa gag gaa atc cga gaa gca ttc cgt<br>Lys Met Lys Asp Thr Asp Ser Glu Glu Glu Ile Arg Glu Ala Phe Arg<br>                        325                              330                            335 | 1008 |
| gtt ttt gac aag gat ggg aac ggc tac atc agc gct gct cag tta cgt<br>Val Phe Asp Lys Asp Gly Asn Gly Tyr Ile Ser Ala Ala Gln Leu Arg<br>                        340                              345                            350 | 1056 |
| cac gtc atg aca aac ctc ggg gag aag tta aca gat gaa gaa gtt gat<br>His Val Met Thr Asn Leu Gly Glu Lys Leu Thr Asp Glu Glu Val Asp<br>                355                            360                            365 | 1104 |
| gaa atg ata agg gaa gca gat atc gat ggt gat ggc caa gta aac tat<br>Glu Met Ile Arg Glu Ala Asp Ile Asp Gly Asp Gly Gln Val Asn Tyr<br>370                                  375                              380 | 1152 |
| gaa gag ttt gta caa atg atg aca gca aag ggg ggg aag agg cgc tgg<br>Glu Glu Phe Val Gln Met Met Thr Ala Lys Gly Gly Lys Arg Arg Trp<br>385                                  390                              395                   400 | 1200 |
| aag aaa aac ttc att gcc gtc agc gct gcc aac cgg ttc aag aag atc<br>Lys Lys Asn Phe Ile Ala Val Ser Ala Ala Asn Arg Phe Lys Lys Ile<br>                        405                              410                            415 | 1248 |
| tcc gag ctc atg gtg agc aag ggc gag gag ctg ttc acc ggg gtg gtg<br>Ser Glu Leu Met Val Ser Lys Gly Glu Glu Leu Phe Thr Gly Val Val<br>                    420                              425                            430 | 1296 |
| ccc atc ctg gtc gag ctg gac ggc gac gta aac ggc cac aag ttc agc<br>Pro Ile Leu Val Glu Leu Asp Gly Asp Val Asn Gly His Lys Phe Ser<br>                435                            440                            445 | 1344 |
| gtg tcc ggc gag ggc gag ggc gat gcc acc tac ggc aag ctg acc ctg<br>Val Ser Gly Glu Gly Glu Gly Asp Ala Thr Tyr Gly Lys Leu Thr Leu<br>450                                  455                              460 | 1392 |
| aag ttc atc tgc acc acc ggc aag ctg ccc gtg ccc tgg ccc acc ctc<br>Lys Phe Ile Cys Thr Thr Gly Lys Leu Pro Val Pro Trp Pro Thr Leu<br>465                                  470                              475                     480 | 1440 |
| gtg acc acc ctg acc tac ggc gtg cag tgc ttc agc cgc tac ccc gac<br>Val Thr Thr Leu Thr Tyr Gly Val Gln Cys Phe Ser Arg Tyr Pro Asp<br>                        485                              490                            495 | 1488 |
| cac atg aag cag cac gac ttc ttc aag tcc gcc atg ccc gaa ggc tac<br>His Met Lys Gln His Asp Phe Phe Lys Ser Ala Met Pro Glu Gly Tyr<br>                    500                              505                            510 | 1536 |
| gtc cag gag cgc acc atc ttc ttc aag gac gac ggc aac tac aag acc<br>Val Gln Glu Arg Thr Ile Phe Phe Lys Asp Asp Gly Asn Tyr Lys Thr<br>                515                            520                            525 | 1584 |
| cgc gcc gag gtg aag ttc gag ggc gac acc ctg gtg aac cgc atc gag<br>Arg Ala Glu Val Lys Phe Glu Gly Asp Thr Leu Val Asn Arg Ile Glu<br>530                                  535                              540 | 1632 |
| ctg aag ggc atc gac ttc aag gag gac ggc aac atc ctg ggg cac aag<br>Leu Lys Gly Ile Asp Phe Lys Glu Asp Gly Asn Ile Leu Gly His Lys<br>545                                  550                              555                   560 | 1680 |
| ctg gag tac aac tac aac agc cac aac gtc tat atc atg gcc gac aag<br>Leu Glu Tyr Asn Tyr Asn Ser His Asn Val Tyr Ile Met Ala Asp Lys<br>                        565                              570                            575 | 1728 |
| cag aag aac ggc atc aag gtg aac ttc aag atc cgc cac aac atc gag<br>Gln Lys Asn Gly Ile Lys Val Asn Phe Lys Ile Arg His Asn Ile Glu<br>                    580                              585                            590 | 1776 |
| gac ggc agc gtg cag ctc gcc gac cac tac cag cag aac acc ccc atc<br>Asp Gly Ser Val Gln Leu Ala Asp His Tyr Gln Gln Asn Thr Pro Ile<br>                595                            600                            605 | 1824 |

```
ggc gac ggc ccc gtg ctg ctg ccc gac aac cac tac ctg agc acc cag    1872
Gly Asp Gly Pro Val Leu Leu Pro Asp Asn His Tyr Leu Ser Thr Gln
    610             615                 620 tcc gcc ctg agc aaa gac ccc aac gag aag cgc gat cac atg gtc ctg    1920
Ser Ala Leu Ser Lys Asp Pro Asn Glu Lys Arg Asp His Met Val Leu
625             630                 635                 640 ctg gag ttc gtg acc gcc gcc ggg atc act ctc ggc aag gac gag ctg    1968
Leu Glu Phe Val Thr Ala Ala Gly Ile Thr Leu Gly Lys Asp Glu Leu
                645                 650                 655 taa                                                                1971

<210> SEQ ID NO 8
<211> LENGTH: 656
<212> TYPE: PRT
<213> ORGANISM: Aequorea victoria

<400> SEQUENCE: 8

Met Leu Leu Pro Val Pro Leu Leu Gly Leu Leu Gly Ala Ala Ala
 1               5                   10                  15

Asp Val Ser Lys Gly Glu Glu Leu Phe Thr Gly Val Val Pro Ile Leu
            20                  25                  30

Val Glu Leu Asp Gly Asp Val Asn Gly His Lys Phe Ser Val Ser Gly
        35                  40                  45

Glu Gly Glu Gly Asp Ala Thr Tyr Gly Lys Leu Thr Leu Lys Phe Ile
    50                  55                  60

Cys Thr Thr Gly Lys Leu Pro Val Pro Trp Pro Thr Leu Val Thr Thr
65                  70                  75                  80

Leu Thr His Gly Val Gln Cys Phe Ser Arg Tyr Pro Asp His Met Lys
                85                  90                  95

Gln His Asp Phe Phe Lys Ser Ala Met Pro Glu Gly Tyr Val Gln Glu
            100                 105                 110

Arg Thr Ile Phe Phe Lys Asp Asp Gly Asn Tyr Lys Thr Arg Ala Glu
        115                 120                 125

Val Lys Phe Glu Gly Asp Thr Leu Val Asn Arg Ile Glu Leu Lys Gly
    130                 135                 140

Ile Asp Phe Lys Glu Asp Gly Asn Ile Leu Gly His Lys Leu Glu Tyr
145                 150                 155                 160

Asn Phe Asn Ser His Asn Val Tyr Ile Met Ala Asp Lys Gln Lys Asn
                165                 170                 175

Gly Ile Lys Val Asn Phe Lys Ile Arg His Asn Ile Glu Asp Gly Ser
            180                 185                 190

Val Gln Leu Ala Asp His Tyr Gln Gln Asn Thr Pro Ile Gly Asp Gly
        195                 200                 205

Pro Val Leu Leu Pro Asp Asn His Tyr Leu Ser Thr Gln Ser Ala Leu
    210                 215                 220

Ser Lys Asp Pro Asn Glu Lys Arg Asp His Met Val Leu Leu Glu Phe
225                 230                 235                 240

Val Thr Ala Ala Arg Met His Asp Gln Leu Thr Glu Glu Gln Ile Ala
                245                 250                 255

Glu Phe Lys Glu Ala Phe Ser Leu Phe Asp Lys Asp Gly Asp Gly Thr
            260                 265                 270

Ile Thr Thr Lys Glu Leu Gly Thr Val Met Arg Ser Leu Gly Gln Asn
        275                 280                 285

Pro Thr Glu Ala Glu Leu Gln Asp Met Ile Asn Glu Val Asp Ala Asp
    290                 295                 300
```

Gly Asn Gly Thr Ile Tyr Phe Pro Glu Phe Leu Thr Met Met Ala Arg
305                 310                 315                 320

Lys Met Lys Asp Thr Asp Ser Glu Glu Ile Arg Glu Ala Phe Arg
            325                 330                 335

Val Phe Asp Lys Asp Gly Asn Gly Tyr Ile Ser Ala Ala Gln Leu Arg
            340                 345                 350

His Val Met Thr Asn Leu Gly Glu Lys Leu Thr Asp Glu Glu Val Asp
            355                 360                 365

Glu Met Ile Arg Glu Ala Asp Ile Asp Gly Asp Gly Gln Val Asn Tyr
370                 375                 380

Glu Glu Phe Val Gln Met Met Thr Ala Lys Gly Gly Lys Arg Arg Trp
385                 390                 395                 400

Lys Lys Asn Phe Ile Ala Val Ser Ala Ala Asn Arg Phe Lys Lys Ile
                405                 410                 415

Ser Glu Leu Met Val Ser Lys Gly Glu Glu Leu Phe Thr Gly Val Val
            420                 425                 430

Pro Ile Leu Val Glu Leu Asp Gly Asp Val Asn Gly His Lys Phe Ser
            435                 440                 445

Val Ser Gly Glu Gly Gly Asp Ala Thr Tyr Gly Lys Leu Thr Leu
450                 455                 460

Lys Phe Ile Cys Thr Thr Gly Lys Leu Pro Val Pro Trp Pro Thr Leu
465                 470                 475                 480

Val Thr Thr Leu Thr Tyr Gly Val Gln Cys Phe Ser Arg Tyr Pro Asp
            485                 490                 495

His Met Lys Gln His Asp Phe Phe Lys Ser Ala Met Pro Glu Gly Tyr
            500                 505                 510

Val Gln Glu Arg Thr Ile Phe Phe Lys Asp Asp Gly Asn Tyr Lys Thr
            515                 520                 525

Arg Ala Glu Val Lys Phe Glu Gly Asp Thr Leu Val Asn Arg Ile Glu
530                 535                 540

Leu Lys Gly Ile Asp Phe Lys Glu Asp Gly Asn Ile Leu Gly His Lys
545                 550                 555                 560

Leu Glu Tyr Asn Tyr Asn Ser His Asn Val Tyr Ile Met Ala Asp Lys
            565                 570                 575

Gln Lys Asn Gly Ile Lys Val Asn Phe Lys Ile Arg His Asn Ile Glu
            580                 585                 590

Asp Gly Ser Val Gln Leu Ala Asp His Tyr Gln Gln Asn Thr Pro Ile
            595                 600                 605

Gly Asp Gly Pro Val Leu Leu Pro Asp Asn His Tyr Leu Ser Thr Gln
            610                 615                 620

Ser Ala Leu Ser Lys Asp Pro Asn Glu Lys Arg Asp His Met Val Leu
625                 630                 635                 640

Leu Glu Phe Val Thr Ala Ala Gly Ile Thr Leu Gly Lys Asp Glu Leu
                645                 650                 655

<210> SEQ ID NO 9
<211> LENGTH: 26
<212> TYPE: PRT
<213> ORGANISM: Oryctolagus cuniculus

<400> SEQUENCE: 9

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

```
<210> SEQ ID NO 10
<211> LENGTH: 20
<212> TYPE: PRT
<213> ORGANISM: Meleagris gallopavo

<400> SEQUENCE: 10

Ala Arg Arg Lys Trp Gln Lys Thr Gly His Ala Val Arg Ala Ile Gly
1               5                   10                  15

Arg Leu Ser Ser
            20

<210> SEQ ID NO 11
<211> LENGTH: 20
<212> TYPE: PRT
<213> ORGANISM: Rattus norvegicus

<400> SEQUENCE: 11

Ala Arg Arg Lys Leu Lys Gly Ala Ile Leu Thr Thr Met Leu Ala Thr
1               5                   10                  15

Arg Asn Phe Ser
            20

<210> SEQ ID NO 12
<211> LENGTH: 17
<212> TYPE: PRT
<213> ORGANISM: Gallus gallus

<400> SEQUENCE: 12

Gly Val Arg Asn Ile Lys Ser Met Trp Glu Lys Gly Asn Val Phe Ser
1               5                   10                  15

Ser

<210> SEQ ID NO 13
<211> LENGTH: 20
<212> TYPE: PRT
<213> ORGANISM: Rattus norvegicus

<400> SEQUENCE: 13

Ala Arg Arg Lys Leu Lys Ala Ala Val Lys Ala Val Val Ala Ser Ser
1               5                   10                  15

Arg Leu Gly Ser
            20

<210> SEQ ID NO 14
<211> LENGTH: 26
<212> TYPE: PRT
<213> ORGANISM: Oryctolagus cuniculus

<400> SEQUENCE: 14

Phe Met Asn Asn Trp Glu Val Tyr Lys Leu Leu Ala His Ile Arg Pro
1               5                   10                  15

Pro Ala Pro Lys Ser Gly Ser Tyr Thr Val
            20                  25

<210> SEQ ID NO 15
<211> LENGTH: 24
<212> TYPE: PRT
<213> ORGANISM: Bos taurus
```

-continued

```
<400> SEQUENCE: 15

Ala Arg Lys Glu Val Ile Arg Asn Lys Ile Arg Ala Ile Gly Lys Met
1               5                   10                  15

Ala Arg Val Phe Ser Val Leu Arg
            20

<210> SEQ ID NO 16
<211> LENGTH: 26
<212> TYPE: PRT
<213> ORGANISM: Oryctolagus cuniculus

<400> SEQUENCE: 16

Leu Arg Arg Leu Ile Asp Ala Tyr Ala Phe Arg Ile Tyr Gly His Trp
1               5                   10                  15

Val Lys Lys Gly Gln Gln Gln Asn Arg Gly
            20                  25

<210> SEQ ID NO 17
<211> LENGTH: 27
<212> TYPE: PRT
<213> ORGANISM: Oryctolagus cuniculus

<400> SEQUENCE: 17

Arg Gly Lys Phe Lys Val Ile Cys Leu Thr Val Leu Ala Ser Val Arg
1               5                   10                  15

Ile Tyr Tyr Gln Tyr Arg Arg Val Lys Pro Gly
            20                  25

<210> SEQ ID NO 18
<211> LENGTH: 28
<212> TYPE: PRT
<213> ORGANISM: Homo sapiens

<400> SEQUENCE: 18

Leu Arg Arg Gly Gln Ile Leu Trp Phe Arg Gly Leu Asn Arg Ile Gln
1               5                   10                  15

Thr Gln Ile Lys Val Val Asn Ala Phe Ser Ser Ser
            20                  25

<210> SEQ ID NO 19
<211> LENGTH: 21
<212> TYPE: PRT
<213> ORGANISM: Bos taurus

<400> SEQUENCE: 19

Arg Arg Lys His Leu Gln Arg Pro Ile Phe Arg Leu Arg Cys Leu Val
1               5                   10                  15

Lys Gln Leu Glu Lys
            20

<210> SEQ ID NO 20
<211> LENGTH: 21
<212> TYPE: PRT
<213> ORGANISM: Bos taurus

<400> SEQUENCE: 20

Thr Glu Lys Met Trp Gln Arg Leu Lys Gly Ile Leu Arg Cys Leu Val
1               5                   10                  15

Lys Gln Leu Glu Lys
            20
```

```
<210> SEQ ID NO 21
<211> LENGTH: 23
<212> TYPE: PRT
<213> ORGANISM: Rattus norvegicus

<400> SEQUENCE: 21

Lys Arg Arg Ala Ile Gly Phe Lys Lys Leu Ala Glu Ala Val Lys Phe
1               5                   10                  15

Ser Ala Lys Leu Met Gly Gln
            20

<210> SEQ ID NO 22
<211> LENGTH: 28
<212> TYPE: PRT
<213> ORGANISM: Bos taurus

<400> SEQUENCE: 22

Ile Lys Pro Ala Lys Arg Met Lys Phe Lys Thr Val Cys Tyr Leu Leu
1               5                   10                  15

Val Gln Leu Met His Cys Arg Lys Met Phe Lys Ala
            20                  25

<210> SEQ ID NO 23
<211> LENGTH: 20
<212> TYPE: PRT
<213> ORGANISM: Bordetella pertussin

<400> SEQUENCE: 23

Ile Asp Leu Leu Trp Lys Ile Ala Arg Ala Gly Ala Arg Ser Ala Val
1               5                   10                  15

Gly Thr Glu Ala
            20

<210> SEQ ID NO 24
<211> LENGTH: 27
<212> TYPE: PRT
<213> ORGANISM: Homo sapiens

<400> SEQUENCE: 24

Lys Ala His Lys Ala Ala Thr Lys Ile Gln Ala Ser Phe Arg Gly His
1               5                   10                  15

Ile Thr Arg Lys Lys Leu Lys Gly Glu Lys Lys
            20                  25

<210> SEQ ID NO 25
<211> LENGTH: 24
<212> TYPE: PRT
<213> ORGANISM: Homo sapiens

<400> SEQUENCE: 25

Lys Thr Ala Ser Pro Trp Lys Ser Ala Arg Leu Met Val His Thr Val
1               5                   10                  15

Ala Thr Phe Asn Ser Ile Lys Glu
            20

<210> SEQ ID NO 26
<211> LENGTH: 25
<212> TYPE: PRT
<213> ORGANISM: Rattus norvegicus
```

```
<400> SEQUENCE: 26

Lys Lys Lys Lys Lys Arg Phe Ser Phe Lys Ser Phe Lys Leu Ser
  1               5                  10                  15

Gly Phe Ser Phe Lys Lys Ser Lys Lys
                20                  25

<210> SEQ ID NO 27
<211> LENGTH: 24
<212> TYPE: PRT
<213> ORGANISM: Mus musculus

<400> SEQUENCE: 27

Lys Lys Lys Lys Lys Phe Ser Phe Lys Lys Pro Phe Lys Leu Ser Gly
  1               5                  10                  15

Leu Ser Phe Lys Arg Asn Arg Lys
                20

<210> SEQ ID NO 28
<211> LENGTH: 31
<212> TYPE: PRT
<213> ORGANISM: Homo sapiens

<400> SEQUENCE: 28

Lys Gln Gln Lys Glu Lys Thr Arg Trp Leu Asn Thr Pro Asn Thr Tyr
  1               5                  10                  15

Leu Arg Val Asn Val Ala Asp Glu Val Gln Arg Asn Met Gly Ser
                20                  25                  30

<210> SEQ ID NO 29
<211> LENGTH: 21
<212> TYPE: PRT
<213> ORGANISM: Mus musculus

<400> SEQUENCE: 29

Lys Asp Gln Val Ala Asn Ser Ala Phe Gln Glu Arg Leu Arg Lys His
  1               5                  10                  15

Gly Leu Glu Val Ile
                20

<210> SEQ ID NO 30
<211> LENGTH: 21
<212> TYPE: PRT
<213> ORGANISM: HIV-1

<400> SEQUENCE: 30

Tyr His Arg Leu Arg Asp Leu Leu Leu Ile Val Lys Arg Ile Val Glu
  1               5                  10                  15

Leu Leu Gly Arg Arg
                20

<210> SEQ ID NO 31
<211> LENGTH: 23
<212> TYPE: PRT
<213> ORGANISM: Bos taurus

<400> SEQUENCE: 31

Gln Gln Leu Ala Thr Leu Ile Gln Lys Thr Tyr Arg Gly Trp Arg Cys
  1               5                  10                  15

Arg Thr His Tyr Gln Leu Met
                20
```

```
<210> SEQ ID NO 32
<211> LENGTH: 24
<212> TYPE: PRT
<213> ORGANISM: Mus musculus

<400> SEQUENCE: 32

Arg Ala Ala Cys Ile Arg Ile Gln Lys Thr Ile Arg Gly Trp Leu Leu
1               5                   10                  15

Arg Lys Arg Tyr Leu Cys Met Gln
            20

<210> SEQ ID NO 33
<211> LENGTH: 14
<212> TYPE: PRT
<213> ORGANISM: Vespa crabro

<400> SEQUENCE: 33

Ile Asn Leu Lys Ala Leu Ala Ala Leu Ala Lys Lys Ile Leu
1               5                   10

<210> SEQ ID NO 34
<211> LENGTH: 26
<212> TYPE: PRT
<213> ORGANISM: Apis mellifera

<400> SEQUENCE: 34

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 35
<211> LENGTH: 30
<212> TYPE: PRT
<213> ORGANISM: Bos taurus

<400> SEQUENCE: 35

His Ser Gln Gly Thr Phe Thr Ser Asp Tyr Ser Lys Tyr Leu Asp
1               5                   10                  15

Ser Arg Arg Ala Gln Asp Phe Val Gln Trp Leu Met Asn Thr
            20                  25                  30

<210> SEQ ID NO 36
<211> LENGTH: 27
<212> TYPE: PRT
<213> ORGANISM: Sus scrofa

<400> SEQUENCE: 36

His Ser Asp Gly Thr Phe Thr Ser Glu Leu Ser Arg Leu Arg Asp Ser
1               5                   10                  15

Ala Arg Leu Gln Arg Leu Leu Gln Gly Leu Val
            20                  25

<210> SEQ ID NO 37
<211> LENGTH: 28
<212> TYPE: PRT
<213> ORGANISM: Homo sapiens

<400> SEQUENCE: 37

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25
```

```
<210> SEQ ID NO 38
<211> LENGTH: 33
<212> TYPE: PRT
<213> ORGANISM: Sus scrofa

<400> SEQUENCE: 38

Tyr Ala Asp Gly Thr Phe Ile Ser Asp Tyr Ser Ala Ile Met Asn Lys
 1               5                  10                  15

Ile Arg Gln Gln Asp Phe Val Asn Trp Leu Leu Ala Gln Gln Gln Lys
            20                  25                  30

Ser

<210> SEQ ID NO 39
<211> LENGTH: 17
<212> TYPE: PRT
<213> ORGANISM: Artificial Sequence
<220> FEATURE:
<223> OTHER INFORMATION: Calmodulin binding peptide-2

<400> SEQUENCE: 39

Lys Leu Trp Lys Lys Leu Leu Lys Leu Leu Lys Lys Leu Leu Lys Leu
 1               5                  10                  15

Gly

<210> SEQ ID NO 40
<211> LENGTH: 5
<212> TYPE: PRT
<213> ORGANISM: Artificial Sequence
<220> FEATURE:
<223> OTHER INFORMATION: Linker moiety; sequence repeated indefinitely

<400> SEQUENCE: 40

Gly Gly Gly Gly Ser
 1               5

<210> SEQ ID NO 41
<211> LENGTH: 12
<212> TYPE: PRT
<213> ORGANISM: Artificial Sequence
<220> FEATURE:
<223> OTHER INFORMATION: Linker moiety

<400> SEQUENCE: 41

Gly Lys Ser Ser Gly Ser Gly Ser Glu Ser Lys Ser
 1               5                  10

<210> SEQ ID NO 42
<211> LENGTH: 14
<212> TYPE: PRT
<213> ORGANISM: Artificial Sequence
<220> FEATURE:
<223> OTHER INFORMATION: Linker moiety

<400> SEQUENCE: 42

Gly Ser Thr Ser Gly Ser Gly Lys Ser Ser Glu Gly Lys Gly
 1               5                  10

<210> SEQ ID NO 43
<211> LENGTH: 18
<212> TYPE: PRT
<213> ORGANISM: Artificial Sequence
<220> FEATURE:
<223> OTHER INFORMATION: Linker moiety
```

-continued

<400> SEQUENCE: 43

Gly Ser Thr Ser Gly Ser Gly Lys Ser Ser Glu Gly Ser Gly Ser Thr
1               5                   10                  15

Lys Gly

<210> SEQ ID NO 44
<211> LENGTH: 14
<212> TYPE: PRT
<213> ORGANISM: Artificial Sequence
<220> FEATURE:
<223> OTHER INFORMATION: Linker moiety

<400> SEQUENCE: 44

Gly Ser Thr Ser Gly Ser Gly Lys Ser Ser Glu Gly Lys Gly
1               5                   10

<210> SEQ ID NO 45
<211> LENGTH: 18
<212> TYPE: PRT
<213> ORGANISM: Artificial Sequence
<220> FEATURE:
<223> OTHER INFORMATION: Linker moiety

<400> SEQUENCE: 45

Gly Ser Thr Ser Gly Ser Gly Lys Pro Gly Ser Gly Glu Gly Ser Thr
1               5                   10                  15

Lys Gly

<210> SEQ ID NO 46
<211> LENGTH: 14
<212> TYPE: PRT
<213> ORGANISM: Artificial Sequence
<220> FEATURE:
<223> OTHER INFORMATION: Linker moiety

<400> SEQUENCE: 46

Glu Gly Lys Ser Ser Gly Ser Gly Ser Glu Ser Lys Glu Phe
1               5                   10

<210> SEQ ID NO 47
<211> LENGTH: 5
<212> TYPE: PRT
<213> ORGANISM: Homo sapiens

<400> SEQUENCE: 47

Lys Lys Lys Arg Lys
1               5

<210> SEQ ID NO 48
<211> LENGTH: 26
<212> TYPE: PRT
<213> ORGANISM: Homo sapiens

<400> SEQUENCE: 48

Met Leu Arg Thr Ser Ser Leu Phe Thr Arg Arg Val Gln Pro Ser Leu
1               5                   10                  15

Phe Arg Asn Ile Leu Arg Leu Gln Ser Thr
                20                  25

<210> SEQ ID NO 49
<211> LENGTH: 4
<212> TYPE: PRT
<213> ORGANISM: Homo sapiens

```
<400> SEQUENCE: 49

Lys Asp Glu Leu
 1

<210> SEQ ID NO 50
<211> LENGTH: 3
<212> TYPE: PRT
<213> ORGANISM: Saccharomyces cerevisiae

<400> SEQUENCE: 50

Ser Lys Phe
 1

<210> SEQ ID NO 51
<211> LENGTH: 4
<212> TYPE: PRT
<213> ORGANISM: Homo sapiens
<220> FEATURE:
<221> NAME/KEY: VARIANT
<222> LOCATION: (1)...(4)
<223> OTHER INFORMATION: Xaa = Any Amino Acid

<400> SEQUENCE: 51

Cys Ala Ala Xaa
 1

<210> SEQ ID NO 52
<211> LENGTH: 2
<212> TYPE: PRT
<213> ORGANISM: Homo sapiens

<400> SEQUENCE: 52

Cys Cys
 1

<210> SEQ ID NO 53
<211> LENGTH: 3
<212> TYPE: PRT
<213> ORGANISM: Homo sapiens
<220> FEATURE:
<221> NAME/KEY: VARIANT
<222> LOCATION: (1)...(3)
<223> OTHER INFORMATION: Xaa = Any Amino Acid

<400> SEQUENCE: 53

Cys Xaa Cys
 1

<210> SEQ ID NO 54
<211> LENGTH: 4
<212> TYPE: PRT
<213> ORGANISM: Homo sapiens
<220> FEATURE:
<221> NAME/KEY: VARIANT
<222> LOCATION: (1)...(4)
<223> OTHER INFORMATION: Xaa = Any Amino Acid

<400> SEQUENCE: 54

Cys Cys Xaa Xaa
 1

<210> SEQ ID NO 55
<211> LENGTH: 10
<212> TYPE: PRT
<213> ORGANISM: Homo sapiens
```

-continued

```
<400> SEQUENCE: 55

Pro Lys Lys Lys Arg Lys Val Glu Asp Pro
1               5                   10

<210> SEQ ID NO 56
<211> LENGTH: 18
<212> TYPE: PRT
<213> ORGANISM: Rattus norvegicus

<400> SEQUENCE: 56

Met Leu Leu Pro Val Pro Leu Leu Leu Gly Leu Leu Gly Leu Ala Ala
1               5                   10                  15

Ala Asp
```

FLUORESCENT PROTEIN SENSORS FOR DETECTION OF ANALYTES

This application is a continuation of U.S. application Ser. No. 09/554,000, filed Apr. 20, 2000 (now U.S. Pat. No. 7,060, 869) which is a continuation of U.S. application Ser. No. 08/818,252, filed Mar. 14, 1997 (now U.S. Pat. No. 6,197, 928).

STATEMENT AS TO FEDERALLY SPONSORED RESEARCH

This invention was made with Government support under Grant No. NS27177, awarded by the National Institutes of Health. The Government has certain rights in this invention.

BACKGROUND OF THE INVENTION

The invention relates to fluorescent protein sensors for detecting and quantifying analytes.

Measurement of an analyte concentration in vitro or in vivo by non-invasive techniques can help elucidate the physiological function of the analyte. This can also aid in identifying changes that occur in a cell or organism in response to physiological stimuli. For example, cyclic AMP can be detected by fluorescence resonance energy transfer between a separately labeled proteins that associate with each other but are not covalently attached to each other. See, U.S. Pat. No. 5,439, 797.

For example, many effects of $Ca^{2+}$ in cells are mediated by $Ca^{2+}$ binding to calmodulin (CaM), which causes CaM to bind and activate target proteins or peptide sequences. Based on the NMR solution structure of CaM bound to the 26-residue M13 $Ca^{2+}$-binding peptide of myosin light-chain kinase, Porumb et al. fused the C-terminus of CaM via a Gly-Gly spacer to the M13. $Ca^{2+}$ binding switches the resulting hybrid protein (CaM-M13) from a dumbbell-like extended form to a compact globular form similar to the CaM-M13 intermolecular complex. See, Porumb, T., et al., Prot. Engineering 7:109-115 (1994).

Fluorescent $Ca^{2+}$ indicators such as fura-2, indo-1, fluo-3, and Calcium-Green have been the mainstay of intracellular $Ca^{2+}$ measurement and imaging. See, for example, U.S. Pat. No. 4,603,209 and U.S. Pat. No. 5,049,673. These relatively low molecular weight indicators can suffer from many technical problems relating to ester loading, leakage of the dyes from the cell, compartmentation in organelles, and perturbation of the indicators by cellular constituents. Although the $Ca^{2+}$ indicating photoprotein aequorin is targetable, the photoresponse to $Ca^{2+}$ is low since it is chemiluminescent. Moreover, aequorins need to incorporate exogenous coelenterazine.

SUMMARY OF THE INVENTION

This invention provides fluorescent indicators and methods for using them to determine the concentration of an analyte both in vitro and in vivo. In one aspect, the fluorescent indicator includes a binding protein moiety, a donor fluorescent protein moiety, and an acceptor fluorescent protein moiety. The binding protein moiety has an analyte-binding region which binds an analyte and causes the indicator to change conformation upon exposure to the analyte. The donor fluorescent protein moiety is covalently coupled to the binding protein moiety. The acceptor fluorescent protein moiety is covalently coupled to the binding protein moiety. In the fluorescent indicator, the donor moiety and the acceptor moiety change position relative to each other when the analyte binds to the analyte-binding region, altering fluorescence resonance energy transfer between the donor moiety and the acceptor moiety when the donor moiety is excited.

The donor fluorescent protein moiety and the acceptor fluorescent protein moiety can be Aequorea-related fluorescent protein moieties. Preferably, the donor fluorescent protein moiety is P4-3, EBFP, or W1B, and the acceptor fluorescent protein moiety is S65T, EGFP, or 10c.

In preferred embodiments, the indicator further includes the target peptide moiety and a linker moiety that covalently couples the binding protein and the target peptide moiety. The binding protein moiety further includes a peptide-binding region for binding the target peptide moiety. The binding protein moiety can be covalently coupled to the donor fluorescent protein moiety and the target peptide moiety can be covalently coupled to the acceptor fluorescent protein moiety.

The indicator can be a single polypeptide. In preferred embodiments, one of the donor fluorescent protein moiety or the acceptor fluorescent protein moiety is covalently coupled to the carboxy terminus of the single polypeptide and the other of the donor fluorescent protein moiety or the acceptor fluorescent protein moiety is covalently coupled to the amino terminus of the single polypeptide.

The indicator can include a localization sequence. The localization sequence can be a nuclear localization sequence, an endoplasmic reticulum localization sequence, a peroxisome localization sequence, a mitochondrial import sequence, a mitochondrial localization sequence, or a localized protein.

In preferred embodiments, the linker moiety is a peptide moiety. The linker moiety can include between about 1 amino acid residue and about 20 amino acid residues. The linker moiety can be -Gly-Gly-.

Preferably, the binding protein moiety is calmodulin, a calmodulin-related protein moiety, cGMP-dependent protein kinase, a steroid hormone receptor, a ligand binding domain of a steroid hormone receptor, protein kinase C, inositol-1,4, 5-triphosphate receptor, or recoverin. A calmodulin-related protein moiety is derived from calmodulin that has been modified to have a different binding affinity for calcium or a target peptide moiety.

Most preferably, the binding protein moiety is calmodulin or a calmodulin-related protein moiety. In these embodiments, the target peptide moiety can be a subsequence of a calmodulin-binding domain of M13, smMLCKp, CaMKII, Caldesmon, Calspermin, Calcineurin, PhK5, PhK13, C28W, 59-kDa PDE, 60-kDa PDE, NO-30, AC-28, Bordetella pertussis AC, Neuro-modulin, Spectrin, MARCKS, F52, .beta.-Adducin, HSP90a, HIV-1 gp160, BBMHBI, Dilute MHC, Mastoparan, Melittin, Glucagon, Secretin, VIP, GIP, or Model Peptide CBP2. Preferably, the target peptide moiety is M13.

In another aspect, the invention features a fluorescent indicator including a target peptide moiety, a binding protein moiety, a linker moiety, a donor fluorescent protein moiety covalently coupled to the binding protein moiety, and an acceptor fluorescent protein moiety covalently coupled to the binding protein moiety. The binding protein moiety has an analyte-binding region which binds an analyte and causes the indicator to change conformation upon exposure to the analyte. The linker moiety covalently couples the binding protein and the target peptide moiety and is a peptide moiety. The binding protein moiety has a peptide-binding region for binding the target peptide moiety. The indicator is a single polypeptide.

In another aspect, the invention features a method for determining the concentration of an analyte in a sample. The method includes the steps of contacting the sample with a fluorescent indicator having a donor fluorescent protein moiety, binding protein moiety, and acceptor protein moiety, exciting the donor moiety, and determining the degree of fluorescence resonance energy transfer in the sample corresponding to the concentration of the analyte in the sample.

In preferred embodiments, the step of determining the degree of fluorescence resonance energy transfer in the sample includes measuring light emitted by the acceptor fluorescent protein moiety. In other preferred embodiments, determining the degree of fluorescence resonance energy transfer in the sample includes measuring light emitted from the donor fluorescent protein moiety, measuring light emitted from the acceptor fluorescent protein moiety, and calculating a ratio of the light emitted from the donor fluorescent protein moiety and the light emitted from the acceptor fluorescent protein moiety. In yet other preferred embodiments, determining the degree of fluorescence resonance energy transfer in the sample includes measuring the excited state lifetime of the donor moiety.

The method can further include the steps of determining the concentration of the analyte at a first time after contacting the sample with the fluorescence indicator, determining the concentration of the analyte at a second time after contacting the sample with the fluorescence indicator, and calculating the difference in the concentration of the analyte at the first time and the second time, whereby the difference in the concentration of the analyte in the sample reflects a change in concentration of the analyte present in the sample.

In other embodiments, the method can further include the step of contacting the sample with a compound between the first time and the second time, whereby a difference in the concentration of the analyte in the sample between the first time and the second time indicates that the compound alters the presence of the analyte.

In preferred embodiments, the sample includes an intact cell and the contacting step includes incorporating the fluorescent indicator into the cell. The step of incorporating the fluorescent indicator into the cell can include transfecting the cell with an expression vector comprising expression control sequences operably linked to a nucleic acid sequence coding for the expression of the fluorescent indicator. The preferred analyte is calcium.

In yet another aspect, the invention features an isolated nucleic acid sequence which encodes the fluorescent indicator. In preferred embodiments, an expression vector or a transgenic non-human animal includes the nucleic acid sequence.

In another aspect, the invention features an expression vector including expression control sequences operatively linked to a nucleic acid sequence coding for the expression of the fluorescent indicator. The expression vector can be adapted for function in a prokaryotic cell or a eukaryotic cell.

In another aspect of the invention, a host cell transfected with an expression vector can include an expression control sequence operatively linked to a sequence coding for the expression of the fluorescent indicator. The cell can be a prokaryote, such as *E. coli*, or a eukaryotic cell, such as a yeast cell or mammalian cell.

In another aspect, the invention features a transgenic non-human animal having a phenotype characterized by expression of the nucleic acid sequence coding for the expression of the fluorescent indicator. The phenotype is conferred by a transgene contained in the somatic and germ cells of the animal. The animal can be a mouse.

In another aspect, the invention features a method for producing a transgenic non-human animal having a phenotype characterized by expression of the nucleic acid sequence coding for the expression of the fluorescent indicator. The method includes the steps of: (a) introducing a transgene into a zygote of an animal, the transgene comprising a DNA construct encoding the fluorescent indicator; (b) transplanting the zygote into a pseudopregnant animal; (c) allowing the zygote to develop to term; and (d) identifying at least one transgenic offspring containing the transgene. The step of introducing of the transgene into the embryo can be by introducing an embryonic stem cell containing the transgene into the embryo, or infecting the embryo with a retrovirus containing the transgene.

"Peptide" refers to a polymer in which the monomers are amino acid residues which are joined together through amide bonds, alternatively referred to as a polypeptide. A "single polypeptide" is a continuous peptide that constitutes the protein. When the amino acids are alpha-amino acids, either the L-optical isomer or the D-optical isomer can be used, the L-isomers being preferred. Additionally, unnatural amino acids such as beta-alanine, phenylglycine, and homo-arginine are meant to be included. Commonly encountered amino acids which are not gene-encoded can also be used in the present invention, although preferred amino acids are those that are encodable. For a general review, see, for example, Spatola, A. F., in Chemistry and Biochemistry of Amino Acids, Peptides and Proteins, B. Weinstein, ed., Marcel Dekker, N.Y., p. 267 (1983).

"Fluorescent protein" refers to any protein capable of emitting light when excited with appropriate electromagnetic radiation. Fluorescent proteins include proteins having amino acid sequences that are either natural or engineered, such as the fluorescent proteins derived from *Aequorea*-related fluorescent proteins.

In FRET, the "donor fluorescent protein moiety" and the "acceptor fluorescent protein moiety" are selected so that the donor and acceptor moieties exhibit fluorescence resonance energy transfer when the donor moiety is excited. One factor to be considered in choosing the donor/acceptor fluorescent protein moiety pair is the efficiency of FRET between the two moieties. Preferably, the efficiency of FRET between the donor and acceptor moieties is at least 10%, more preferably at least 50%., and most preferably at least 80%. The efficiency of FRET can be tested empirically using the methods described herein and known in the art, particularly, using the conditions set forth in the Examples.

"Covalently coupled" refers to a covalent bond or other covalent linkage between two moieties. The covalent linkage can include a diradical moiety linking to two moieties.

"Binding protein" refers to a protein capable of binding an analyte. Preferred binding proteins change conformation upon binding the analyte. "Target peptide" refers to a peptide that can bind to the binding protein. The target peptide can be a subsequence of a peptide that binds to the binding protein.

"Analyte" refers to a molecule or ion in solution that binds to the binding protein, causing it to change conformation. Preferably, the analyte binds reversibly to the binding protein.

"Moiety" refers to a radical of a molecule that is attached to another radical of the indicator. Thus, a "fluorescent protein moiety" is the radical of a fluorescent protein coupled to a binding protein moiety or a linker moiety, a "binding protein moiety" is a radical of a binding protein coupled to a fluorescent protein moiety, a "target peptide moiety" is a radical of a target peptide of the binding protein, and a "linker moiety"

refers to the radical of a molecular linker that is ultimately coupled to both the donor and acceptor fluorescent protein moieties.

"Operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. The term "control sequences" is intended to include, at a minimum, components whose presence can influence expression, and can also include additional components whose presence is advantageous, for example, leader sequences and fusion partner sequences.

"Polynucleotide" refers to a polymeric form of nucleotides of at least 10 bases in length. The nucleotides can be ribonucleotides, deoxynucleotides, or modified forms of either type of nucleotide. The term includes single and double stranded forms of DNA.

The invention can have one or more of the following advantages. Ligand-induced conformational changes can be monitored by FRET if, for example, the amino and carboxy termini of the binding protein are fused to a donor and acceptor GFP. This approach has several advantages over the usual covalent labeling with fluorescent probes. The fluorescent indicator can be generated in situ by gene transfer into the cells or organisms. This approach avoids the need to express and purify large quantities of soluble recombinant protein, purify and label it in vitro, microinject it back into cells. The fluorescent indicator can be targeted to cellular structures. The sites of fusion between the moieties of the fluorescent indicator are exactly defined, giving a molecularly homogenous product without relying on elaborate protein chemistry. In addition, the chromophore of GFP is fixed in the protein. See, Ormo, M., et al., Science 273:1392-1395 (1996). If the GFP donor and acceptor are fused to a host protein rigidly, minor changes in the relative orientation of the ends of the latter would alter FRET. In contrast, most conventional fluorescent labels are attached by flexible linkers that at least partially decouple the fluorophore orientation from that of the protein to which it is attached, limiting the sensitivity of the FRET measurement.

Other features or advantages of the present invention will be apparent from the following detailed description of the invention, and also from the claims.

BRIEF DESCRIPTION OF THE DRAWINGS

FIG. 6b is a graph depicting temporal changes in the emission ratio of cameleon-2 for each of the HeLa cells shown in FIG. 6a.

FIG. 7 depicts the nucleotide sequence (SEQ ID NO:1) and amino acid sequence (SEQ ID NO:2) of cameleon-2.

FIG. 8 depicts the nucleotide sequence (SEQ ID NO:3) and amino acid sequence (SEQ ID NO:4) of cameleon-2nu.

FIG. 9 depicts the nucleotide sequence (SEQ ID NO:5) and amino acid sequence (SEQ ID NO:6) of cameleon-3.

FIG. 10 is a list depicting the nucleotide sequence (SEQ ID NO:7) and amino acid sequence of cameleon-3er (SEQ ID NO:8).

DETAILED DESCRIPTION

A fluorescent indicator that utilizes fluorescent resonance energy transfer ("FRET") to measure the concentration of an analyte includes two fluorescent protein moieties having emission and excitation spectra that render one a donor fluorescent protein moiety and the other an acceptor fluorescent protein moiety. The fluorescent protein moieties are chosen such that the excitation spectrum of one of the moieties (the acceptor fluorescent protein moiety) overlaps with the emission spectrum of the excited protein moiety (the donor fluorescent protein moiety). The donor and acceptor fluorescent protein moieties are bound to a binding protein moiety that changes conformation upon binding the analyte. The change in conformation leads to a change in relative position and orientation of the donor and acceptor fluorescent protein moieties, thereby altering the relative amounts of fluorescence from the two fluorescent protein moieties when the donor is excited by irradiation. In particular, binding of the analyte changes the ratio of the amount of light emitted by the donor and acceptor fluorescent protein moieties. The ratio between the two emission wavelengths provides a measure of the concentration of the analyte in the sample, which is based in part on the binding affinity of the binding protein moiety and the analyte.

Figure 1:
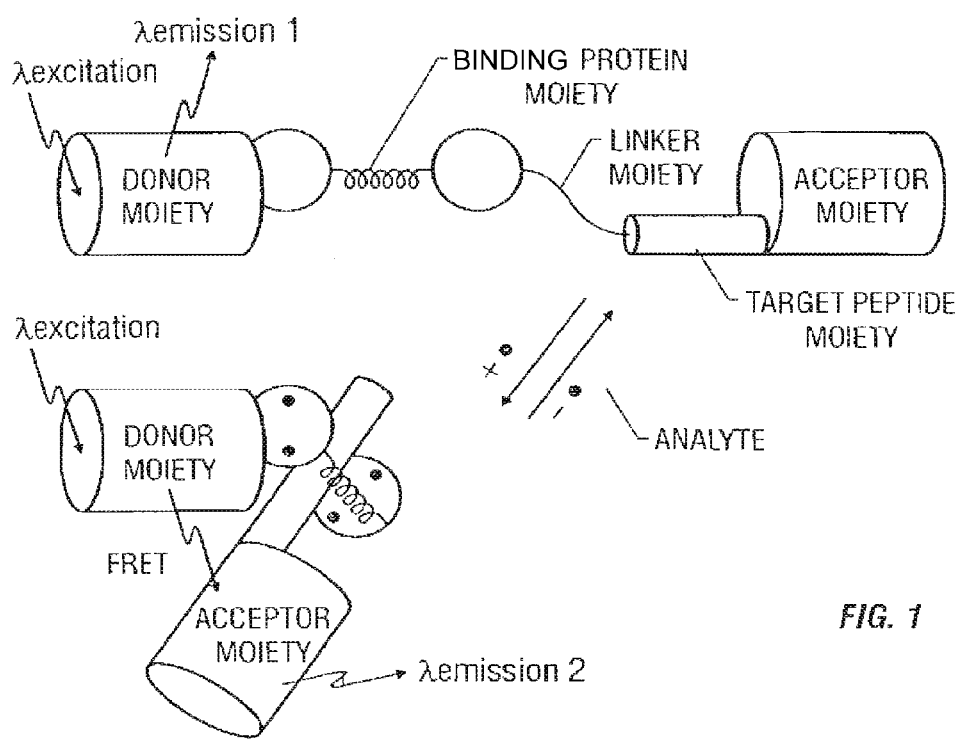
FIG. 1 is a schematic diagram depicting a fluorescent indicator that measures the concentration of an analyte by fluorescence resonance energy transfer.

Referring to FIG. 1, the donor fluorescent protein moiety is covalently linked to a first region (e.g., the amino terminus) of the binding protein moiety, and the acceptor fluorescent protein moiety is covalently linked to a second region (e.g., the carboxy terminus) of the binding protein moiety such that the donor and acceptor moieties move closer together upon binding the analyte. Alternatively, the donor and acceptor moieties can move farther apart upon binding the analyte. In one embodiment, depicted in FIG. 1, the acceptor moiety is covalently bonded to a target peptide moiety that also binds to the binding protein moiety and the target peptide moiety is covalently bonded to the binding protein moiety by a linker moiety. The linker moiety is flexible enough to allow the target peptide moiety to bind to the binding protein moiety. The donor moiety is excited by light of appropriate intensity within the excitation spectrum of the donor moiety ($\lambda_{excitation}$). The donor moiety emits the absorbed energy as fluorescent light ($\lambda_{emission\ 1}$). When the acceptor fluorescent protein moiety is positioned to quench the donor moiety in the excited state, the fluorescence energy is transferred to the acceptor moiety which can emit fluorescent light ($\lambda_{emission\ 2}$). FRET can be manifested as a reduction in the intensity of the fluorescent signal from the donor moiety ($\lambda_{emission\ 1}$), reduction in the lifetime of the excited state of the donor moiety, or emission of fluorescent light at the longer wavelengths (lower energies) characteristic of the acceptor moiety ($\lambda_{emission\ 2}$). When the conformation of the binding protein moiety changes upon binding the analyte, the fluorescent protein moieties come closer together (or physically separate), and FRET is increased (or decreased) accordingly.

The efficiency of FRET depends on the separation distance and the orientation of the donor and acceptor fluorescent protein moieties. For example, the Forster equation describes the efficiency of excited state energy transfer, based in part on the fluorescence quantum yield of the donor moiety and the energetic overlap with the acceptor moiety. The Forster equation is:

$$E=(F_0-F)/F_0=R_0^6/(R^6+R_0^6)$$

where E is the efficiency of FRET, F and $F_0$ are the fluorescence intensities of the donor moiety in the presence and absence of the acceptor, respectively, and R is the distance between the donor moiety and the acceptor moiety.

The characteristic distance $R_0$ at which FRET is 50% efficient depends on the quantum yield of the donor moiety (i.e., the shorter-wavelength fluorophore), the extinction coefficient of the acceptor moiety (i.e., the longer-wavelength fluorophore), and the overlap between the emission spectrum of the donor moiety and the excitation spectrum of the acceptor moiety. $R_0$ is given (in Å) by $$R_0=9.79\times10^3(K^2QJn^{-4})^{1/6}$$

where $K^2$ is an orientation factor having an average value close to 0.67 for freely mobile donors and acceptors, Q is the quantum yield of the unquenched donor moiety, n is the refractive index of the medium separating the donor moiety and the acceptor moiety, and J is the overlap integral. J can be quantitatively expressed as the degree of spectral overlap between the donor moiety and the acceptor moiety according to the equation:

$$J=\int_0^\infty \epsilon_\lambda F_\lambda \lambda^4 d\lambda / \int_0^\infty F_\lambda d\lambda$$

where $\epsilon_\lambda (M^{-1}\ cm^{-1})$ is the molar absorptivity of the acceptor and $F_\lambda$ is the donor moiety fluorescence intensity at wavelength .lamda. See, for example, Forster, T. Ann Physik 2:55-75 (1948). Tables of spectral overlap integrals are readily available to those working in the field (for example, Berlman, I. B. Energy transfer parameters of aromatic compounds, Academic Press, N.Y. and London (1973)). FRET is a non-destructive spectroscopic method that can monitor proximity and relative angular orientation of fluorophores in living cells. See, for example, Adams, S. R., et al., Nature 349:694-697 (1991), and Gonzalez, J. & Tsien, R. Y. Biophy. J. 69:1272-1280 (1995).

These factors need to be balanced to optimize the efficiency and detectability of FRET from the fluorescent indicator. The emission spectrum of the donor fluorescent protein moiety should overlap as much as possible with the excitation spectrum of the acceptor fluorescent protein moiety to maximize the overlap integral J. Also, the quantum yield of the donor fluorescent protein moiety and the extinction coefficient of the acceptor fluorescent protein moiety should be as large as possible to maximize $R_0$. In addition, the excitation spectra of the donor and acceptor moieties should overlap as little as possible so that a wavelength region can be found at which the donor moiety can be excited selectively and efficiently without directly exciting the acceptor moiety. Direct excitation of the acceptor moiety should be avoided since it can be difficult to distinguish direct emission from fluorescence arising from FRET. Similarly, the emission spectra of the donor and acceptor moieties should have minimal overlap so that the two emissions can be distinguished. High fluorescence quantum yield of the acceptor moiety is desirable if the emission from the acceptor moiety is to be monitored to determine analyte concentration in a sample. In a preferred embodiment, the donor fluorescent protein moiety is excited by ultraviolet (<400 nm) and emits blue light (<500 nm), and the acceptor fluorescent protein moiety is efficiently excited by blue but not by ultraviolet light and emits green light (>500 nm), for example, P4-3 and S65T, respectively.

In another preferred embodiment, the donor fluorescent moiety is excited by violet (400-430 nm) and emits blue-green (450-500 nm) and the acceptor fluorescent moiety is efficiently excited by blue-green (450-500 nm) and emits yellow-green light $\geq 520$ nm), for example WIB and 10C respectively.

The amount of analyte in a sample can be determined by determining the degree of FRET in the sample. Changes in analyte concentration can be determined by monitoring FRET at a first and second time after contact between the sample and the fluorescent indicator and determining the difference in the degree of FRET. The amount of analyte in the sample can be calculated by using a calibration curve established by titration.

The degree of FRET can be determined by any spectral or fluorescence lifetime characteristic of the excited donor moiety. For example, intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor can be monitored.

Preferably, changes in the degree of FRET are determined as a function of the change in the ratio of the amount of fluorescence from the donor and acceptor moieties, a process referred to as "ratioing." Changes in the absolute amount of indicator, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of cleavage than either intensity alone.

Fluorescence in a sample is measured using a fluorometer. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361.

The excited state lifetime of the donor moiety is, likewise, independent of the absolute amount of substrate, excitation intensity, or turbidity or other background absorbances. Its measurement requires equipment with nanosecond time resolution.

Quantum yields of wild-type GFP, S65T, and P4-1 mutants can be estimated by comparison with fluorescein in 0.1 N NaOH as a standard of quantum yield 0.91. J. N. Miller, ed., Standards in Fluorescence Spectrometry, New York: Chapman and Hall (1981). Mutants P4 and P4-3 were likewise compared to 9-aminoacridine in water (quantum yield 0.98).

Any fluorescent protein can be used in the invention, including proteins that fluoresce due intramolecular rearrangements or the addition of cofactors that promote fluorescence. For example, green fluorescent proteins of cnidarians, which act as their energy-transfer acceptors in bioluminescence, are suitable fluorescent proteins for use in the fluorescent indicators. A green fluorescent protein ("GFP") is a protein that emits green light, and a blue fluorescent protein ("BFP") is a protein that emits blue light. GFPs have been isolated from the Pacific Northwest jellyfish, *Aequorea victoria*, the sea pansy, *Renilla reniformis*, and *Phialidium gregarium*. See, Ward, W. W., et al., Photochem. Photobiol., 35:803-808 (1982); and Levine, L. D., et al., Comp. Biochem. Physiol., 72B:77-85 (1982).

A variety of *Aequorea*-related GFPs having useful excitation and emission spectra have been engineered by modifying the amino acid sequence of a naturally occurring GFP from *Aequorea victoria*. See, Prasher, D. C., et. al., Gene, 111:229-233 (1992); Heim, R., et al., Proc. Natl. Acad. Sci., USA, 91:12501-04 (1994); U.S. Ser. No. 08/337,915, filed Nov. 10, 1994; International application PCT/US95/14692, filed Nov. 10, 1995; and U.S. Ser. No. 08/706,408, filed Aug. 30, 1996. The cDNA of GFP can be concatenated with those encoding many other proteins; the resulting fusions often are fluorescent and retain the biochemical features of the partner proteins. See, Cubitt, A. B., et al., Trends Biochem. Sci. 20:448-455 (1995). Mutagenesis studies have produced GFP mutants with shifted wavelengths of excitation or emission. See, Heim, R. & Tsien, R. Y. Current Biol. 6:178-182 (1996). Suitable pairs, for example a blue-shifted GFP mutant P4-3 (Y66H/Y145F) and an improved green mutant S65T can respectively serve as a donor and an acceptor for fluorescence resonance energy transfer (FRET). See, Tsien, R. Y., et al., Trends Cell Biol. 3:242-245 (1993). A fluorescent protein is an *Aequorea*-related fluorescent protein if any contiguous sequence of 150 amino acids of the fluorescent protein has at least 85% sequence identity with an amino acid sequence, either contiguous or non-contiguous, from the wild type *Aequorea* green fluorescent protein. More preferably, a fluorescent protein is an *Aequorea*-related fluorescent protein if any contiguous sequence of 200 amino acids of the fluorescent protein has at least 95% sequence identity with an amino acid sequence, either contiguous or non-contiguous, from the wild type *Aequorea* green fluorescent protein. Similarly, the fluorescent protein can be related to *Renilla* or *Phialidium* wild-type fluorescent proteins using the same standards. Some *Aequorea*-related engineered versions described in Table I. Other variants or mutants are within the scope of the invention as described, for example, in the Examples.

TABLE I

| Clone | Mutation(s) | Excitation max (nm) | Emission max (nm) | Extinction Coefficient $(M^{-1}cm^{-1})$ | Quantum yield |
|---|---|---|---|---|---|
| Wild type | none | 395 (475) | 508 | 21,000 (7,150) | 0.77 |
| P4 | Y66H | 383 | 447 | 13,500 | 0.21 |
| P4-3 | Y66H; Y145F | 381 | 445 | 14,000 | 0.38 |
| W7 | Y66W; N146I M153T V163A N212K | 433 (453) | 475 (501) | 18,000 (17,100) | 0.67 |
| W2 | Y66W; I123V Y145H H148R M153T V163A N212K | 432 (453) | 480 | 10,000 (9,600) | 0.72 |
| S65T | S65T | 489 | 511 | 39,200 | 0.68 |
| P4-1 | S65T; M153A K238E | 504 (396) | 514 | 14,500 (8,600) | 0.53 |
| S65A | S65A | 471 | 504 | | |
| S65C | S65C | 479 | 507 | | |
| S65L | S65L | 484 | 510 | | |
| Y66F | Y66F | 360 | 442 | | |
| Y66W | Y66W | 458 | 480 | | |
| 10c | S65G; V68L S72A; T203Y | 513 | 527 | | |

TABLE I-continued

| Clone | Mutation(s) | Excitation max (nm) | Emission max (nm) | Extinction Coefficient ($M^{-1}cm^{-1}$) | Quantum yield |
|---|---|---|---|---|---|
| W1B | F64L; S65T Y66W; N146I M153T V163A N212K | 432 (453) | 476 (503) | | |
| Emerald | S65T; S72A N149K M153T I167T | 487 | 508 | | |
| Sapphire | S72A; Y145F T203I | 395 | 511 | | |

An additional clone, W1B1 included the following mutations: F64L;S65T; Y66W; F99S; and V163A.

Other fluorescent proteins can be used in the fluorescent indicators, such as, for example, yellow fluorescent protein from *Vibrio fischeri* strain Y-1, Peridinin-chlorophyll a binding protein from the dinoflagellate *Symbiodinium* sp. *phycobiliproteins* from marine cyanobacteria such as *Synechococcus*, e.g., phycoerythrin and phycocyanin, or oat phytochromes from oat reconstructed with phycoerythrobilin. These fluorescent proteins have been described in Baldwin, T. O., et al., Biochemistry 29:5509-5515 (1990), Morris, B. J., et al., Plant Molecular Biology, 24:673-677 (1994), and Wilbanks, S. M., et al., J. Biol. Chem. 268:1226-1235 (1993), and Li et al., Biochemistry 34:7923-7930 (1995).

The efficiency of FRET between the donor and acceptor fluorescent protein moieties can be adjusted by changing ability of the two fluorescent proteins to closely associate. The nature of the binding protein moiety, target peptide moiety, and linker moiety each affect the FRET and the response of the indicator to the analyte. Generally, large conformational changes in the binding protein moiety are desired along with a high affinity for the target peptide moiety.

The binding protein moiety is a protein, or part thereof, that changes conformation upon binding an analyte. Proteins that undergo useful conformation change upon binding an analyte include calmodulin (CaM), cGMP-dependent protein kinase, steroid hormone receptors (or ligand binding domain thereof), protein kinase C, inositol-1,4,5-triphosphate receptor, or recoverin. See, for example, Katzenellenbogen, J. A. & Katzenellenbogen, B. S. Chemistry & Biology 3:529-536 (1996), and Ames, J. B., et al., Curr. Opin. Struct. Biol. 6:432-438 (1996). The binding protein moiety preferably binds target peptides in addition to the analyte. The $Ca^{2+}$-binding affinity of calmodulin can be tuned as reviewed, for example, in Falke, J. J., et al., Quart. Rev. Biophys. 27:219-290 (1994).

The target peptide moiety can contain any of the amino acid sequences in Table II, or a portion thereof with the proviso that the target peptide must bind to the binding protein moiety. The target peptide can be a subsequence of a calmodulin-binding domain. The target peptide moieties listed in Table II are recognized by the binding protein moiety CaM. See, for example, Crivici, A. & Ikura, M. Annu Rev. Biophys. Biomol. Struct. 24:84-116 (1995). The target peptide moiety can be modified to enhance the response of the fluorescent indicator to the analyte. Other target peptide moieties are known in the art for other binding proteins.

TABLE II

| Target[a] | Sequence |
|---|---|
| skMLCK (M13) | KRRWKKNFIAVSAANRFKKISSSGAL (SEQ. ID. NO.: 9) |
| smMLCK (smMLCKp) | ARRKWQKTGHAVRAIGRLSS (SEQ. ID. NO.: 10) |
| CaMKII | ARRKLKGAILTTMLATRNFS (SEQ. ID. NO.: 11) |
| Caldesmon | GVRNIKSMWEKGNVFSS (SEQ. ID. NO.: 12) |
| Calspermin | ARRKLKAAVKAVVASSRLGS (SEQ. ID. NO.: 13) |
| PFK (M11) | FMNNWEVYKLLAHIRPPAPKSGSYTV (SEQ. ID. NO.: 14) |
| Calcineurin | ARKEVIRNKIRAIGKMARVFSVLR (SEQ. ID. NO.: 15) |
| PhK (PhK5) | LRRLIDAYAFRIYGHWVKKGQQQNRG (SEQ. ID. NO.: 16) |
| (PhK13) | RGKFKVICLTVLASVRIYYQYRRVKPG (SEQ. ID. NO.: 17) |
| $Ca^{2+}$-ATPase (C28W) | LRRGQILWFRGLNRIQTQIKVVNAFSSS (SEQ. ID. NO.: 18) |

TABLE II-continued

| Target[a] | Sequence |
|---|---|
| 59-kDa PDE | RRKHLQRPIFRLRCLVKQLEK (SEQ. ID. NO.: 19) |
| 60-kDa PDE | TEKMWQRLKGILRCLVKQLEK (SEQ. ID. NO.: 20) |
| NOS (NO-30) | KRRAIGFKKLAEAVKFSAKLMGQ (SEQ. ID. NO.: 21) |
| Type I AC (AC-28) | IKPAKRMKFKTVCYLLVQLMHCRKMFKA (SEQ. ID. NO.: 22) |
| *Borderella periussis* AC | IDLLWKIARAGARSAVGTEA (SEQ. ID. NO.: 23) |
| Neuromodulin | KAHKAATKIQASFRGHITRKKLKGEKK (SEQ. ID. NO.: 24) |
| Spectrin | KTASPWKSARLMVHTVATFNSIKE (SEQ. ID. NO.: 25) |
| MARCKS | KKKKKRFSFKKSFKLSGFSFKKSKK (SEQ. ID. NO.: 26) |
| F52 or MacMARKS | KKKKKFSFKKPFKLSGLSFKRNRK (SEQ. ID. NO.: 27) |
| β-Adducin | KQQKEKTRWLNTPNTYLRVNVADEVQRNMGS (SEQ. ID. NO.: 28) |
| HSP90a | KDQVANSAFQERLRKHGLEVI (SEQ. ID. NO.: 29) |
| HIV-1 gp160 | YHRLRDLLLIVKRIVELLGRR (SEQ. ID. NO.: 30) |
| BBMHBI | QQLATLIQKTYRGWRCRTHYQLM (SEQ. ID. NO.: 31) |
| Dilute MHC | RAACIRIQKTIRGWLLRKRYLCMQ (SEQ. ID. NO.: 32) |
| Mastoparan | INLKALAALAKKIL (SEQ. ID. NO.: 33) |
| Melittin | GIGAVLKVLTTGLPALISWIKRKRQQ (SEQ. ID. NO.: 34) |
| Glucagon | HSQGTFTTSDYSKYLDSRRAQDFVQWLMNT (SEQ. ID. NO.: 35) |
| Secretin | HSDGTFTSELSRLRDSARLQRLLQGLV (SEQ. ID. NO.: 36) |
| VIP | HSDAVFTDNYTRLRKQMAVKKYLNSILN (SEQ. ID. NO.: 37) |
| GIP | YADGTFISDYSAIMNKIRQQDFVNWLLAQQQKS (SEQ. ID. NO.: 38) |
| Model Peptide CBP2 | KLWKKLLKLLKKLLKLG (SEQ. ID. NO.: 39) |

[a]Abbreviations: AC, adenylyl cyclase;
BBMHCI, brush-border myosin heavy chain-I;
CaMKII, calmodulin kinase II;
CBP2, calmodulin binding peptide-2;
GIP, gastrin inhibitory peptide;
HIV-1 gp160, human immunodeficiency virus envelope glycoprotein 160;
HSP, heat-shock protein;
MARCKS, myristoylated alaminte-rich C kinase substrate;
MHC, myosin heavy chain;
NOS, nitric oxide synthase;
PDE, phosphodiesterase;
PFK, phosphofructokinase;
PhK, phosphorylase kinase;
sk-, smMLCK, skeletal muscle- and smooth muscle-myosin light chain kinase;
VIP, vasoactive intestinal peptide.

The length of the linker moiety is chosen to optimize both FRET and the kinetics and specificity of conformational changes induced by analyte binding. The linker moiety should be long enough and flexible enough to allow the binding protein moiety and target peptide moiety to freely interact and respond to analyte concentration. In order to optimize the FRET effect, the average distance between the donor and acceptor fluorescent protein moieties should become between about 1 nm and about 10 nm, preferably between about 1 nm and about 6 nm, and more preferably between about 1 nm and about 4 nm, when the analyte is bound (or released). If the linker is too short or too stiff, the donor and acceptor protein moieties cannot readily change position. If the linker moiety is too long, the target peptide moiety might not bind to the binding protein moiety effectively. The linker moiety is, preferably, a peptide moiety. The preferred linker moiety is a peptide between about one and 30 amino acid residues in length, preferably between about two and 15 amino acid residues. One preferred linker moiety is a -Gly-Gly-linker.

The linker moiety can include flexible spacer amino acid sequences, such as those known in single-chain antibody research. For example, the linker moiety can be GGGGS (GGGGS)$_n$, (SEQ. ID. NO.: 40) GKSSGSGSESKS, (SEQ. ID. NO.: 41) GSTSGSGKSSEGKG, (SEQ. ID. NO.: 42) GSTSGSGKSSEGSGSTKG, (SEQ. ID. NO.: 43) GSTSGS-GKSSEGKG, (SEQ. ID. NO.: 44) GSTSGSGKPGSGEG-STKG, (SEQ. ID. NO.: 45) or EGKSSGSGSESKEF (SEQ. ID. NO.: 46). Linking moieties are described, for example, in Huston, J. S., et al., PNAS 85:5879-5883 (1988), Whitlow, M., et al., Protein Engineering 6:989-995 (1993), and Newton, D. L., et al., Biochemistry 35:545-553 (1996).

The fluorescent indicators can also include a localization sequence to direct the indicator to particular cellular sites by fusion to appropriate organellar targeting signals or localized host proteins. A polynucleotide encoding a localization sequence, or signal sequence, can be ligated or fused at the 5' terminus of a polynucleotide encoding the fluorescence indicator such that the signal peptide is located at the amino terminal end of the resulting fusion polynucleotide/polypeptide. In the case of eukaryotes, the signal peptide is believed to function to transport the fusion polypeptide across the endoplasmic reticulum. The secretory protein is then transported through the Golgi apparatus, into secretory vesicles and into the extracellular space or, preferably, the external environment. Signal peptides which can be utilized according to the invention include pre-pro peptides which contain a proteolytic enzyme recognition site. Other signal peptides with similar properties to pro-calcitonin described herein are known to those skilled in the art, or can be readily ascertained without undue experimentation.

The localization sequence can be a nuclear localization sequence, an endoplasmic reticulum localization sequence, a peroxisome localization sequence, a mitochondrial localization sequence, or a localized protein. Localization sequences can be targeting sequences which are described, for example, in "Protein Targeting", chapter 35 of Stryer, L., Biochemistry (4th ed.). W. H. Freeman, 1995. The localization sequence can also be a localized protein. Some important localization sequences include those targeting the nucleus (KKKRK), (SEQ. ID. NO.: 47) mitochondrion (amino terminal MLRTSSLFTRRVQPSLFRNILRLQST-),(SEQ. ID. NO.: 48) endoplasmic reticulum (KDEL (SEQ. ID. NO.: 49) at C-terminus, assuming a signal sequence present at N-terminus), peroxisome (SKF (SEQ. ID. NO.: 50) at C-terminus), prenylation or insertion into plasma membrane (CaaX, (SEQ. ID. NO.: 51) CC, (SEQ. ID. NO.: 52) CXC, (SEQ. ID. NO.: 53) or CCXX (SEQ. ID. NO.: 54) at C-terminus), cytoplasmic side of plasma membrane (fusion to SNAP-25), or the Golgi apparatus (fusion to furin).

The fluorescent indicators can be produced as fusion proteins by recombinant DNA technology. Recombinant production of fluorescent proteins involves expressing nucleic acids having sequences that encode the proteins. Nucleic acids encoding fluorescent proteins can be obtained by methods known in the art. For example, a nucleic acid encoding the protein can be isolated by polymerase chain reaction of cDNA from *A. victoria* using primers based on the DNA sequence of *A. victoria* green fluorescent protein. PCR methods are described in, for example, U.S. Pat. No. 4,683,195; Mullis, et al. Cold Spring Harbor Symp. Quant. Biol. 51:263 (1987), and Erlich, ed., PCR Technology, (Stockton Press, N.Y., 1989). Mutant versions of fluorescent proteins can be made by site-specific mutagenesis of other nucleic acids encoding fluorescent proteins, or by random mutagenesis caused by increasing the error rate of PCR of the original polynucleotide with 0.1 mM MnCl$_2$ and unbalanced nucleotide concentrations. See, e.g., U.S. patent application Ser. No. 08/337,915, filed Nov. 10, 1994 or International application PCT/US95/14692, filed Nov. 10, 1995.

The construction of expression vectors and the expression of genes in transfected cells involves the use of molecular cloning techniques also well known in the art. Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., most recent Supplement).

Nucleic acids used to transfect cells with sequences coding for expression of the polypeptide of interest generally will be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods which are well known to those skilled in the art can be used to construct expression vectors containing the fluorescent indicator coding sequence and appropriate transcriptional/translational control signals. These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the CaCl$_2$ method by procedures well known in the art. Alternatively, MgCl$_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

A variety of host-expression vector systems may be utilized to express fluorescent indicator coding sequence. These include but are not limited to microorganisms such as bacteria transformed with recombinant bacteriophage DNA, plasmid DNA or cosmid DNA expression vectors containing a fluorescent indicator coding sequence; yeast transformed with recombinant yeast expression vectors containing the fluorescent indicator coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a fluorescent indicator coding sequence; insect cell systems infected with recombinant virus expression vectors (e.g., baculovirus) containing a fluorescent indicator coding sequence; or animal cell systems infected with recombinant virus expression vectors (e.g., retroviruses, adenovirus, vaccinia virus) containing a fluorescent indicator coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516-544, 1987). For example, when cloning in bacterial systems, inducible promoters such as pL of bacteriophage λ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted fluorescent indicator coding sequence.

In bacterial systems a number of expression vectors may be advantageously selected depending upon the use intended for the fluorescent indicator expressed. For example, when large quantities of the fluorescent indicator are to be produced, vectors which direct the expression of high levels of fusion protein products that are readily purified may be desirable. Those which are engineered to contain a cleavage site to aid in recovering fluorescent indicator are preferred.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp. 516-544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y., Vol. 152, pp. 673-684, 1987; and The Molecular Biology of the Yeast *Saccharomyces*, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, IRL Press, Wash., D.C., 1986). Alternatively, vectors may be used which promote integration of foreign DNA sequences into the yeast chromosome.

In cases where plant expression vectors are used, the expression of a fluorescent indicator coding sequence may be driven by any of a number of promoters. For example, viral promoters such as the 35S RNA and 19S RNA promoters of CaMV (Brisson, et al., Nature 310:511-514, 1984), or the coat protein promoter to TMV (Takamatsu, et al., EMBO J. 6:307-311, 1987) may be used; alternatively, plant promoters such as the small subunit of RUBISCO (Coruzzi, et al., 1984, EMBO J. 3:1671-1680; Broglie, et al., Science 224:838-843, 1984); or heat shock promoters, e.g., soybean hsp17.5-E or hsp17.3-B (Gurley, et al., Mol. Cell. Biol. 6:559-565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, N.Y., Section VIII, pp. 421-463, 1988; and Grierson & Corey, Plant Molecular Biology, 2d Ed., Blackie, London, Ch. 7-9, 1988.

An alternative expression system which could be used to express fluorescent indicator is an insect system. In one such system, *Autographa californica* nuclear polyhedrosis virus (AcNPV) is used as a vector to express foreign genes. The virus grows in *Spodoptera frugiperda* cells. The fluorescent indicator coding sequence may be cloned into non-essential regions (for example, the polyhedrin gene) of the virus and placed under control of an AcNPV promoter (for example the polyhedrin promoter). Successful insertion of the fluorescent indicator coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., J. Viol. 46:584, 1983; Smith, U.S. Pat. No. 4,215,051.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent indicator. Such host cell lines may include but are not limited to CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, the fluorescent indicator coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fluorescent indicator in infected hosts (e.g., see Logan & Shenk, Proc. Natl. Acad. Sci. USA, 81: 3655-3659, 1984). Alternatively, the vaccinia virus 7.5K promoter may be used. (e.g., see, Mackett, et al., Proc. Natl. Acad. Sci. USA, 79: 7415-7419, 1982; Mackett, et al., J. Virol. 49: 857-864, 1984; Panicali, et al., Proc. Natl. Acad. Sci. USA 79: 4927-4931, 1982). Of particular interest are vectors based on bovine papilloma virus which have the ability to replicate as extrachromosomal elements (Sarver, et al., Mol. Cell. Biol. 1: 486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent indicator gene in host cells (Cone & Mulligan, Proc. Natl. Acad. Sci. USA, 81:6349-6353, 1984). High level expression may also be achieved using inducible promoters, including, but not limited to, the metallothionine HA promoter and heat shock promoters.

For long-term, high-yield production of recombinant proteins, stable expression is preferred. Rather than using expression vectors which contain viral origins of replication, host cells can be transformed with the fluorescent indicator cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., Cell, 11: 223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22: 817, 1980) genes can be employed in tk_, hgprt⁻ or aprt cells respectively. Also, antimetabolite resistance can be used as the basis of selection for dhfr, which confers resistance to methotrexate (Wigler, et al., Proc. Natl. Acad. Sci. USA, 77: 3567, 1980; O'Hare, et al., Proc. Natl. Acad. Sci. USA, 8: 1527, 1981); gpt, which confers resistance to mycophenolic acid (Mulligan & Berg, Proc. Natl. Acad. Sci. USA, 78: 2072, 1981; neo, which confers resistance to the aminoglycoside G-418 (Colberre-Garapin, et al., J. Mol. Biol., 150:1, 1981); and hygro, which confers resistance to hygromycin (Santerre, et al., Gene, 30: 147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

DNA sequences encoding the fluorescence indicator polypeptide of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

Recombinant fluorescent protein can be produced by expression of nucleic acid encoding the protein in prokaryotes, such as E. coli or in eukaryotes, such as yeast cells or mammalian cells. The fluorophore of Aequorea-related fluorescent proteins results from cyclization and oxidation of residues 65-67.

The construct can also contain a tag to simplify isolation of the fluorescent indicator. For example, a polyhistidine tag of, e.g., six histidine residues, can be incorporated at the amino terminal end of the fluorescent protein. The polyhistidine tag allows convenient isolation of the protein in a single step by nickel-chelate chromatography.

In a preferred embodiment, the fluorescent indicator is a fusion protein produced by recombinant DNA technology in which a single polypeptide includes a donor moiety, a peptide linker moiety and an acceptor moiety. The donor moiety can be positioned at the amino-terminus relative to the acceptor moiety in the polypeptide. Such a fusion protein has the generalized structure: (amino terminus) donor fluorescent protein moiety—peptide linker moiety—acceptor fluorescent protein moiety (carboxy terminus). Alternatively, the donor moiety can be positioned at the carboxy-terminus relative to the acceptor moiety within the fusion protein. Such a fusion protein has the generalized structure: (amino terminus) acceptor fluorescent protein moiety—peptide linker moiety—donor fluorescent protein moiety (carboxy terminus). The invention also envisions fusion proteins that contain extra amino acid sequences at the amino and/or carboxy termini, for example, polyhistidine tags.

Thus, fluorescent indicators encoded by a recombinant nucleic acid include sequences coding for expression of a donor fluorescent protein moiety, an acceptor fluorescent protein moiety and a peptide linker moiety. The elements are selected so that upon expression into a fusion protein, the donor and acceptor moieties exhibit FRET when the donor moiety is excited. The recombinant nucleic acid can be incorporated into an expression vector comprising expression control sequences operatively linked to the recombinant nucleic acid. The expression vector can be adapted for function in prokaryotes or eukaryotes by inclusion of appropriate promoters, replication sequences, markers, etc.

The expression vector can be transfected into a host cell for expression of the recombinant nucleic acid. Host cells can be selected for high levels of expression in order to purify the fluorescent indicator fusion protein. E. coli is useful for this purpose. Alternatively, the host cell can be a prokaryotic or eukaryotic cell selected to study the activity of an enzyme produced by the cell. In this case, the linker peptide is selected to include an amino acid sequence recognized by the protease. The cell can be, e.g., a cultured cell or a cell in vivo.

A primary advantage of fluorescent indicator fusion proteins is that they are prepared by normal protein biosynthesis, thus completely avoiding organic synthesis and the requirement for customized unnatural amino acid analogs. The constructs can be expressed in *E. coli* in large scale for in vitro assays. Purification from bacteria is simplified when the sequences include polyhistidine tags for one-step purification by nickel-chelate chromatography. Alternatively, the substrates can be expressed directly in a desired host cell for assays in situ.

In another embodiment, the invention provides a transgenic non-human animal that expresses a nucleic acid sequence which encodes the fluorescent indicator.

The "non-human animals" of the invention comprise any non-human animal having nucleic acid sequence which encodes a fluorescent indicator. Such non-human animals include vertebrates such as rodents, non-human primates, sheep, dog, cow, pig, amphibians, and reptiles. Preferred non-human animals are selected from the rodent family including rat and mouse, most preferably mouse. The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster et al., Proc. Natl. Acad. Sci. USA 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

Retroviral infection can also be used to introduce transgene into a non-human animal. The developing non-human embryo can be cultured in vitro to the blastocyst stage. During this time, the blastomeres can be targets for retro viral infection (Jaenich, R., Proc. Natl. Acad. Sci. USA 73:1260-1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., Proc. Natl. Acad. Sci. USA 82:6927-6931, 1985; Van der Putten, et al., Proc. Natl. Acad. Sci. USA 82:6148-6152, 1985). Transfection is easily and efficiently obtained by culturing the blastomeres on a monolayer of virus-producing cells (Van der Putten, supra; Stewart, et al., EMBO J. 6:383-388, 1987). Alternatively, infection can be performed at a later stage. Virus or virus-producing cells can be injected into the blastocoele (D. Jahner et al., Nature 298:623-628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retro viral infection of the midgestation embryo (D Jahner et al., supra).

A third type of target cell for transgene introduction is the embryonal stem cell (ES). ES cells are obtained from pre-implantation embryos cultured in vitro and fused with embryos (M. J. Evans et al. Nature 292:154-156, 1981; M. O. Bradley et al., Nature 309: 255-258, 1984; Gossler, et al., Proc. Natl. Acad. Sci. USA 83: 9065-9069, 1986; and Robertson et al., Nature 322:445-448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., Science 240: 1468-1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode which encodes the fluorescent indicator which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

Without further elaboration, it is believed that one skilled in the art can, based on the description herein, utilize the present invention to its fullest extent. All patents and publications cited herein are hereby incorporated by reference.

Figure 2:
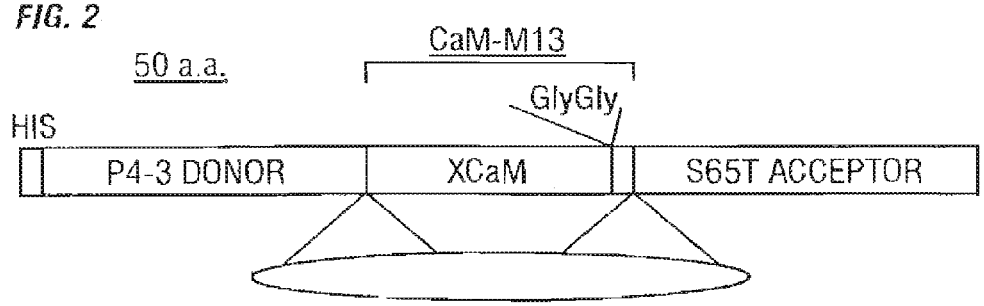
FIG. 2 is a schematic diagram depicting the structure of chimera proteins containing P4-3, CaM-M13, and S65T, where HIS is the amino-terminal tag peptide containing the polyhistidine sequence and XCaM is *Xenopus* calmodulin.

A fluorescent indicator for $Ca^{2+}$ was produced by sandwiching CaM-M13 fusion, described in Porumb, T., et al., Prot. Engineering 7:109-115 (1994), between a blue (P4-3) and a green (S65T) GFP mutant, as illustrated in FIG. 2a. The chimeric cDNA was cloned at BamHI/EcoRI sites of pRSETB (Invitrogen), HIS is the amino-terminal tag peptide containing the polyhistidine sequence and XCaM is *Xenopus* calmodulin. Chimeric proteins incorporating a polyhistidine tag were expressed in *Escherichia coli*, purified by nickel-chelate and size-exclusion chromatography, and their fluorescence characterized. Referring to FIG. 2a, the fluorescent CaM-based indicator ("cameleon-1") readily changes emission color by retracting and extending a long tongue (M13) into and out of the mouth of the CaM.

The amino acid composition of the boundary regions between the CaM-M13 hybrid and GFPs can be important to optimize protein folding and the $Ca^{2+}$-sensitivity of FRET. One particularly sensitive indicator is shown in FIG. 2b. Referring to FIG. 2b, the amino acid and nucleotide sequences of the boundaries between P4-3 and CaM and between M13 and S65T in cameleon-1 are shown. Cameleon-1 has an 11 amino acid deletion at the C-terminus of P4-3 and a 5 amino acid deletion at the C-terminus of M13. Two restriction sites SphI and SacI are underlined, which were utilized to connect the genes of P4-3 and S65T to the CaM-M13 gene, respectively. To facilitate the folding of the GFP that is fused to any other protein, a few glycine residues are usually inserted into the boundary. See, for example, Porumb, T., et al., Prot. Engineering 7:109-115 (1994). Further, glycine residues were not introduced so that P4-3 and S65T were fused rigidly to the CaM and M13, respectively. The rigid fusion leads to more effective transduction of the conformational change of CaM-M13, causing a greater change in FRET efficiency.

Figure 3:
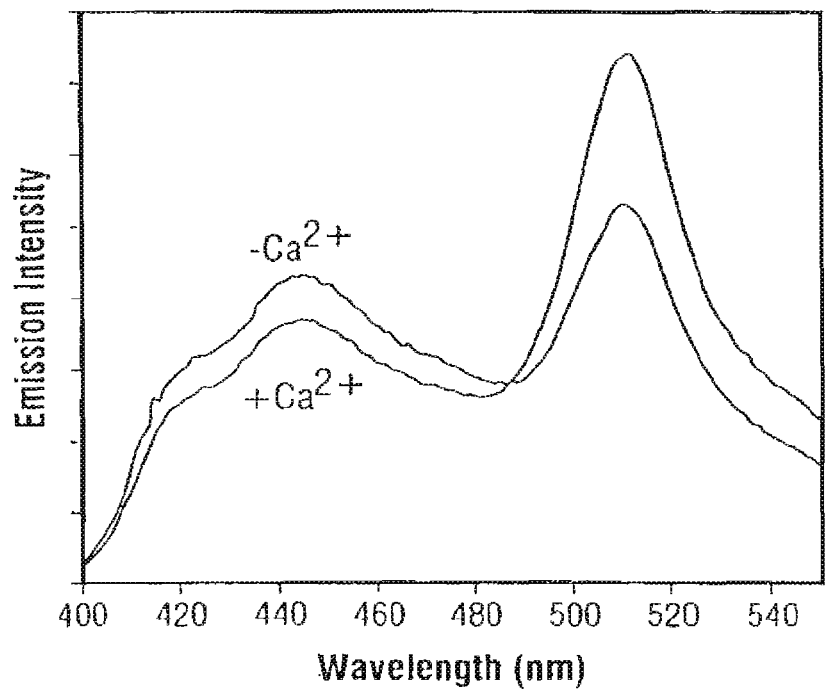
FIG. 3 is a graph depicting the emission spectra of cameleon-1 before and after addition of 2 mM $CaI_2$ to give 1 mM free $Ca^{2+}$.

The fluorescent indicator was efficiently expressed and folded in bacteria and increased its ratio of UV-excited 510 nm to 445 nm emissions by 70% upon binding $Ca^{2+}$, as shown in FIG. 3. The emission spectra of cameleon-1 were measured in 100 mM KCl, 20 mM MOPS, 1 mM EDTA, KOH to pH 7.20, before and after addition of 2 mM $CaCl_2$ to give 1 mM free $Ca^{2+}$. The $Ca^{2+}$ binding to EDTA caused a local acidification of the solution, and a small fraction of the protein was denatured. Thus the spectrum after the $Ca^{2+}$ addition dropped down slightly (compare with FIG. 4a). The decrease in blue and increase in green emission indicated that $Ca^{2+}$ increased the efficiency of FRET from P4-3 to S65T, consistent with the expected decrease in distance between the two ends of the protein. The $Ca^{2+}$ response was fully reversible upon chelation of $Ca^{2+}$.

The $Ca^{2+}$-specificity of the response of cameleon-1 was examined. $Mg^2$ pH, and ionic strength did not alter the emission spectra of either the $Ca^{2+}$-saturated and Ca-unsaturated forms. The emission spectra of saturated and unsaturated cameleon-1 were also not affected by hydrophobic proteins such as bovine serum albumin. Isolated CaM saturated with $Ca^{2+}$ typically becomes sticky with hydrophobic amino acids exposed to the surface. The CaM in cameleon-1, on the other hand, appears to interact preferentially with its intramolecularly-adjacent M13 peptide. The self-contained nature of the system minimizes the possibility that the protein might interact with endogenous CaM-binding sequences in eukaryotic cells.

Figure 4A:
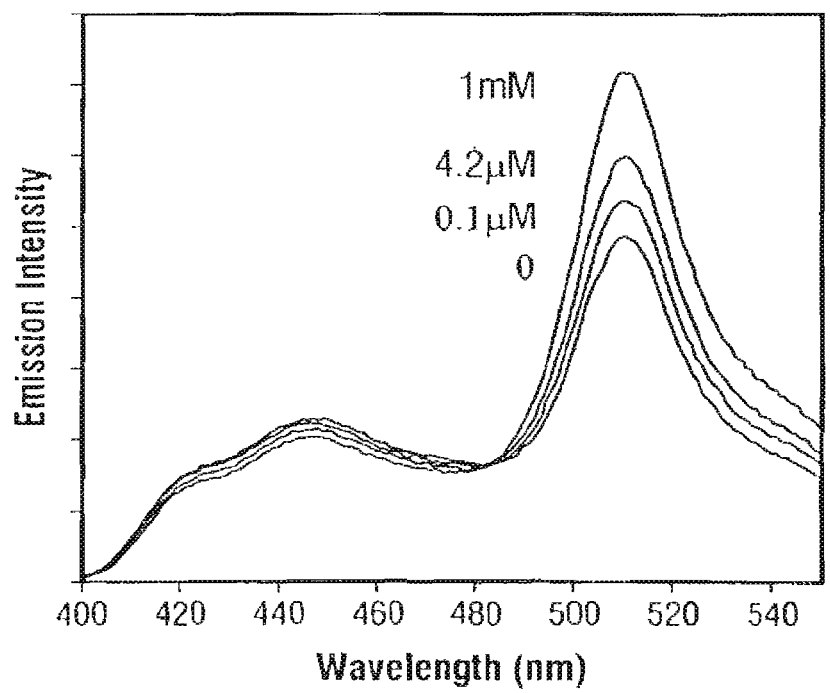
FIG. 4a is a graph depicting the change in emission spectrum of cameleon-1 on titration with $Ca^{2+}$ when excited at 380 nm.
Figure 4B:
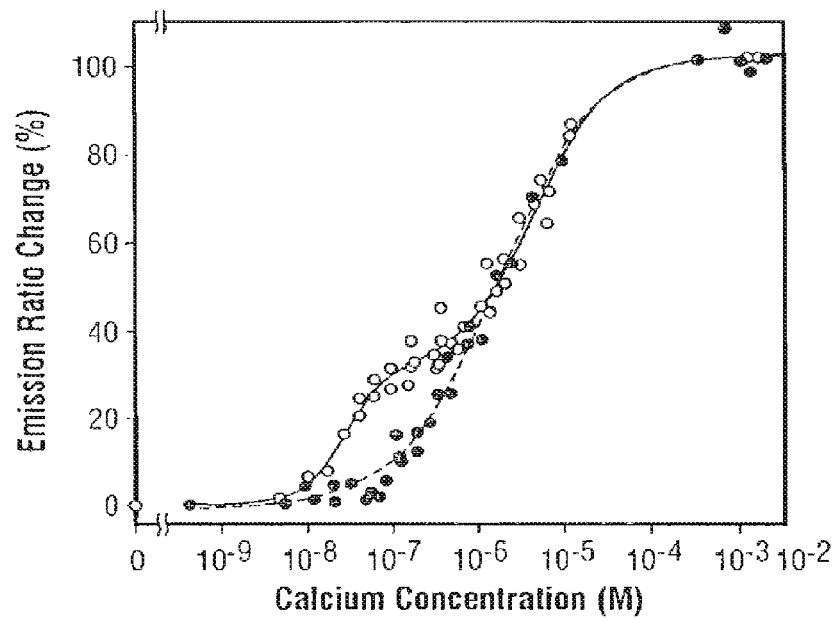
FIG. 4b is a graph depicting $Ca^{2+}$ titration curves of cameleon-1 (open circles) and cameleon-1/E104Q (solid circles).

The $Ca^{2+}$ binding behavior of cameleon-1 was examined. The CaM-M13 hybrid protein without GFPs displayed a biphasic $Ca^{2+}$ binding with two dissociation constants (80 nM and 2 .mu·M). See, Porumb, T., et al., Prot. Engineering 7:109-115 (1994). Titration experiments revealed that the emission ratio of cameleon-1 has a biphasic $Ca^{2+}$ dependency, as shown in FIGS. 4a and 4b. FIG. 4a shows the change in emission spectrum of cameleon-1 on titration with $Ca^{2+}$ when excited at 380 nm. The titration was done using KHHEDTA/KCaHEDTA solutions at pH 7.47. For clarity only two intermediate concentrations of $Ca^{2+}$ are shown.

FIG. 4b shows $Ca^{2+}$ titration curves of cameleon-1 (open circles) and cameleon-1/E104Q (solid circles). Data points were from 4 independent experiments at different pH using $Ca^{2+}$/EGTA and $Ca^{2+}$/HEEDTA systems for each protein. In each experiment, the emission ratio (510/445 nm) change was normalized to the value of full saturation with $Ca^{2+}$, which increased by 60-75% over the value of zero $Ca^{2+}$. The data of cameleon-1/E104Q were fitted to a four parameter logistic function curve (dotted line). The data of cameleon-1 were analysed using a linear combination of 2 four parameter logistic function fits (solid line). The apparent dissociation constants ($K'_{ds}$) for cameleon-1 were 68 nM and 11 µM, and the Hill coefficients were 1.8 and 1.0, respectively. The binding curve can be used to quantify the concentration of $Ca^{2+}$ present in the sample. Because of simulated negative cooperativity, cameleon-1 covers a very wide range of $Ca^{2+}$) concentration, from $<10^{-7}$ to .about.$10^{-3}$ M.

The affinity of the CaM binding protein moiety can be modified. Many site-directed mutations have been studied for their effects on the $Ca^{2+}$ binding and $Ca^{2+}$-induced conformational changes of CaM. See, Maune, J. F., et al., J. Biol. Chem. 267:5286-5295 (1992), and Gao, Z. H., et al., J. Biol. Chem. 268:20096-20104 (1993). For example, a mutant chimera protein with the conserved bidentate glutamic acid at position 12 of the third $Ca^{2+}$ binding loop of the CaM mutated to glutamine (cameleon-1/E104Q) was constructed. The mutation eliminated the high-affinity response of cameleon-1, as indicated in FIG. 4b, (solid circles). Cameleon-1/E104Q showed a monophasic response (K'd, 4.4 .mu·M; Hill coefficient, 0.76), which corresponds closely to the low affinity component of the cameleon-1 FRET response. Other modifications of CaM can be made to tune the $Ca^{2+}$ affinities for particular applications of the fluorescent indicator.

HeLa cells were transfected with the recombinant plasmid (cameleon-1/pcDNA3) to determine whether cameleon-1 can work as a $Ca^{2+}$ indicator in live cells. When the cells were excited with UV, however, the fluorescence of cameleon-1 was hardly detectable, mainly because of the dim fluorescence of the P4-3 component. Expression and folding of GFP at 37.degree. C. in mammalian cells was improved by introducing mammalian codon bias into the cDNA and mutating Phe64 to Leu, as in the commercially available construct "EGFP" (Clonetech), which encodes F64L/S65T with mammalian codons. The same changes were introduced into P4-3 (Y66H/Y145F), which did not change its final fluorescence properties but did improve expression in the HeLa cells. The improved blue mutant ("EBFP") and EGFP substituted P4-3 and S65T, respectively, in cameleon-1 to make cameleon-2, shown in FIG. 5, where Kz is Kozak's consensus sequence (M. Kozak, J. Cell Biol. 108:229-241 (1989). The nucleotide sequence (SEQ ID NO:1) and amino acid sequence (SEQ ID NO:2) of cameleon-2 are shown in FIG. 7.

Figure 5:
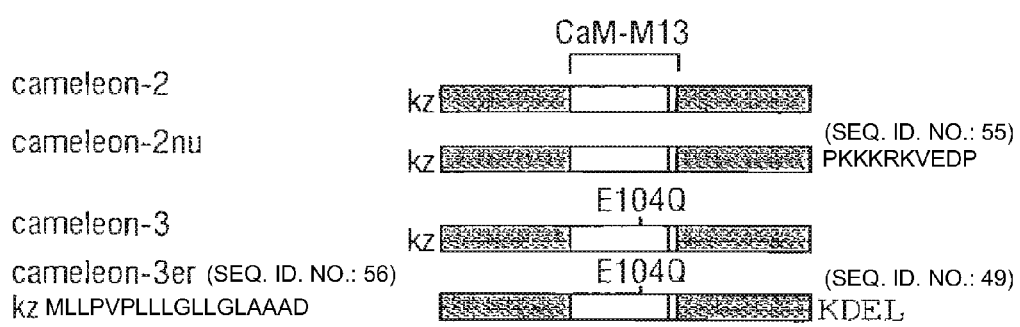
FIG. 5 is a schematic diagram depicting the structures of cameleon-2 and cameleon-3, and their derivatives, cameleon-2nu (SEQ. ID. NO.: 55) and cameleon-3er (SEQ. ID. NO.: 49), where Kz (SEQ. ID. NO.: 56) is Kozak's consensus sequence.

The E104Q mutation which afforded low $Ca^{2+}$ affinity in cameleon-1 was also introduced into cameleon-2; the resulting chimera protein (cameleon-2/E104Q) cameleon-3, also shown in FIG. 5. The nucleotide sequence (SEQ ID NO:5) and amino acid sequence (SEQ ID NO:6) of cameleon-3 are shown in FIG. 9.

Figure 6A:
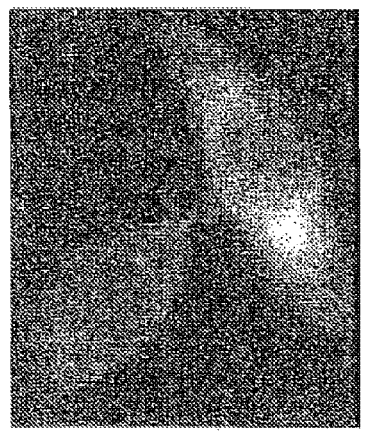
FIG. 6a is a digital fluorescence image depicting fluorescence of cameleon-2 localized to the cytosol of HeLa cells, where the bar is 10 .mu·m.

Significant emission signals were observed from both the EBFP and EGFP in the cells expressing cameleon-2 or cameleon-3. Referring to FIG. 6a, fluorescence of cameleon-2 localized to the cytosol of HeLa cells. The fluorescence was uniformly distributed in the cytosolic compartment but excluded from the nucleus, as expected for a protein of 74 kDa without localization sequences or targeting signals. The image was taken using a 330WB80 (excitation filter) and a 535DF45 (emission filter). The bar is 10 .mu·m.

Figure 6B:
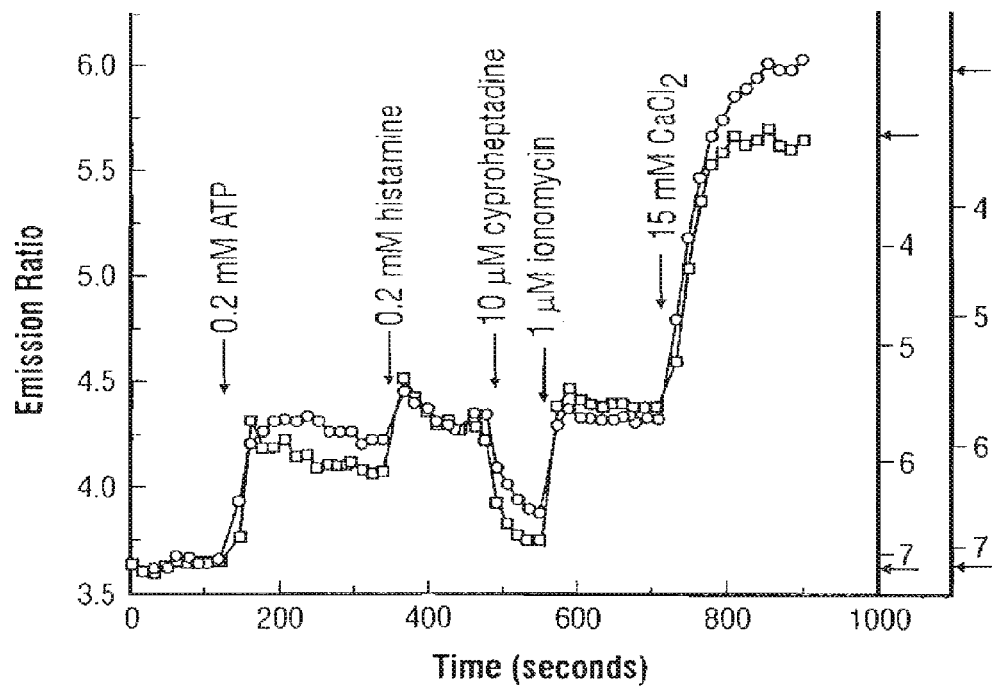

FIG. 6b shows time courses of the spatially averaged green: blue emission ratios from two individual HeLa cells expressing cameleon-2. The two cells shown in FIG. 6a were excited by UV (330WB80) and monitored every 15 seconds by digital imaging microscopy. See, for example, Tsien, R. Y. & Harootunian, A. T. Cell Calcium, 11:93-109 (1990). The emission bands (440DF40 and 535DF45) over the cytoplasmic regions were alternately sampled. In situ calibration was performed for each of the cells. The pre-stimulation ratio (arrowhead) was assumed to be 50 nM, and $R_{max}$ (arrow) the value after saturation with $Ca^{2+}$. The calculated values for pcas 7, 6, 5, 4 are indicated by horizontal bars on the right side of the panel.

Elevation of cytosolic $Ca^{2+}$ concentration by saturating doses of ATP (as a purinergic agonist) and histamine produced significant increases in the emission ratio. Blockage of the histamine receptor by the antagonist cyproheptadine caused a rapid decrease in ratio, indicating the reversible behavior of the indicator. Addition of ionomycin followed by a high concentration (15 mM) of extracellular $Ca^{2+}$ gave a large increase of the ratio (70-80% increase of the initial ratio value), which should correspond to the maximal ratio $R_{max}$. Assuming the lowest ratio observed before stimulation represents the $R_{min}$, calibration for free $Ca^{2+}$ concentration can be performed. See, Adams, S. R., et al., in Fluorescent and Luminescent Probes for Biological Activity (ed. Mason, W. T.) (Academic Press, 1993).

By contrast, cameleon-3, which lacks the high affinity component of $Ca^{2+}$ binding to CaM, did not detect the changes in cytosolic $Ca^{2+}$ concentration signals due to ATP or histamine, but gave a similar $R_{max}$ in response to ionomycin and 20 mM extracellular $Ca^{2+}$. Cameleon-3 is less sensitive to and buffers cytosolic $Ca^{2+}$ to a lesser extent than does cameleon-2. The probable high $Ca^{2+}$ dissociation rate of cameleon-3 is advantageous for tracking rapid $Ca^{2+}$ release kinetics. The in vitro study revealed that the cameleon indicators show a relatively fast cellular response to $Ca^{2+}$ concentration changes.

Figure 6C:
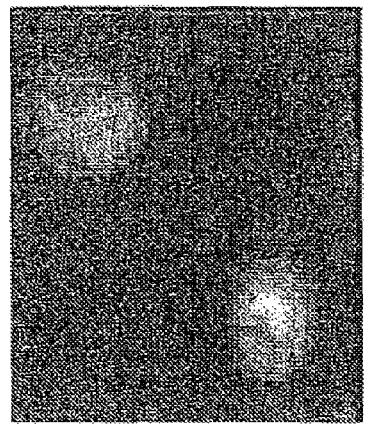
FIG. 6c is a digital fluorescence image depicting fluorescence of cameleon-2nu localized to the nuclei of HeLa cells, where the bar is 10 .mu·m.
Figure 6D:
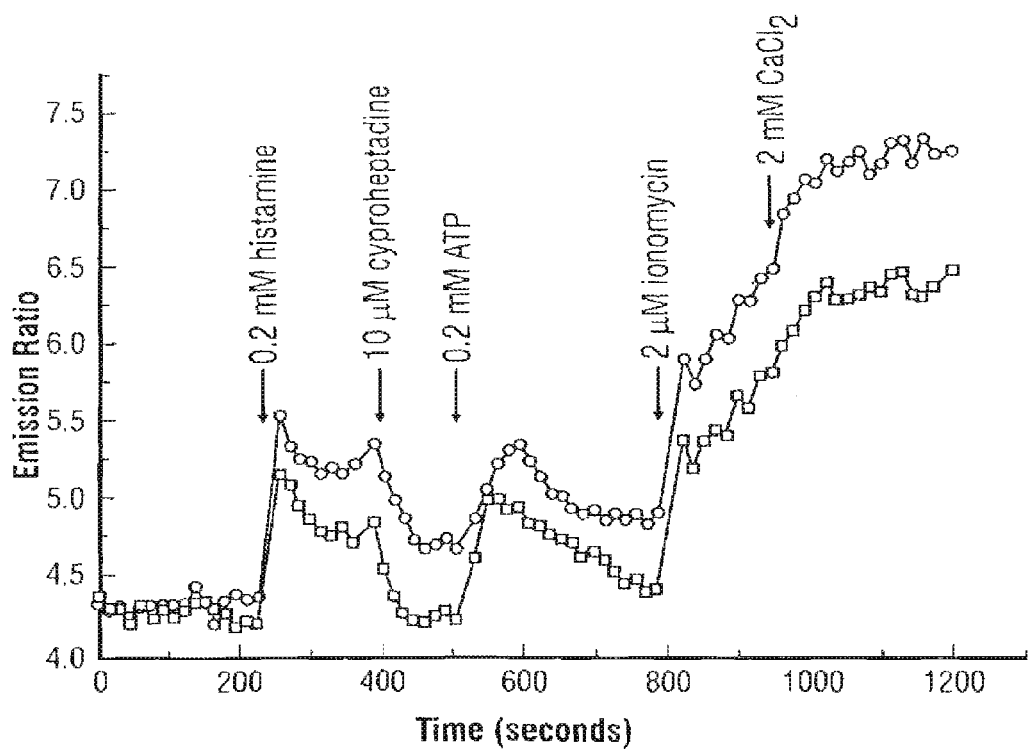
FIG. 6d is a graph depicting temporal changes in the emission ratio of cameleon-2nu in the two nuclei shown in FIG. 6c.

Addition of a nuclear localization sequence to cameleon-2 yielded a $Ca^{2+}$ indicator, cameleon-2nu, shown in FIG. 5. The nucleotide sequence (SEQ ID NO:3) and amino acid sequence (SEQ ID NO:4) of cameleon-2nu are shown in FIG. 8. The fluorescence of cameleon-2nu was localized to nuclei, as depicted in FIG. 6c. The time course of $Ca^{2+}$ concentrations in nuclei was followed (FIG. 6d) and was similar to the results obtained in the cytosol (FIG. 6b).

Figure 6E:
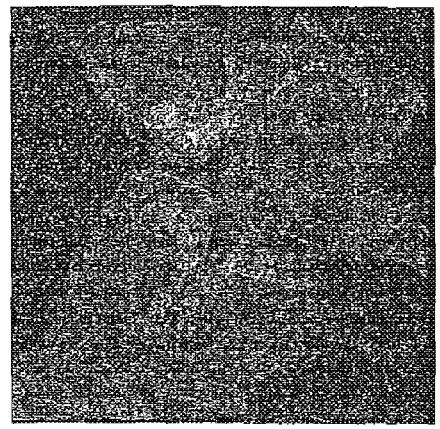
FIG. 6e is a digital fluorescence image depicting fluorescence of cameleon-3er in transfected HeLa cells, where the bar is 10 .mu·m.

Agonist-induced changes in the free $Ca^{2+}$ concentration inside the endoplasmic reticulum in intact cells were similarly monitored. The low-affinity indicator cameleon-3 was engineered to reside in the lumen of endoplasmic reticulum (ER) (cameleon-3er) (FIG. 5) by addition of a localization sequence at the amino terminus and a KDEL signal for ER retention at the carboxy terminus of the fluorescent indicator. The nucleotide sequence (SEQ ID NO:7) and amino acid sequence of cameleon-3er (SEQ ID NO:8) are shown in FIG. 10. Reticular patterns of fluorescence were seen in HeLa cells expressing the protein. FIG. 6e is a digital fluorescence image of cameleon-3er in transfected HeLa cells. The image was obtained with a cooled CCD camera system with a 480DF30 (excitation filter) and a 535DF45 (emission filter). The bar is 10 .mu.m.

Figure 6F:
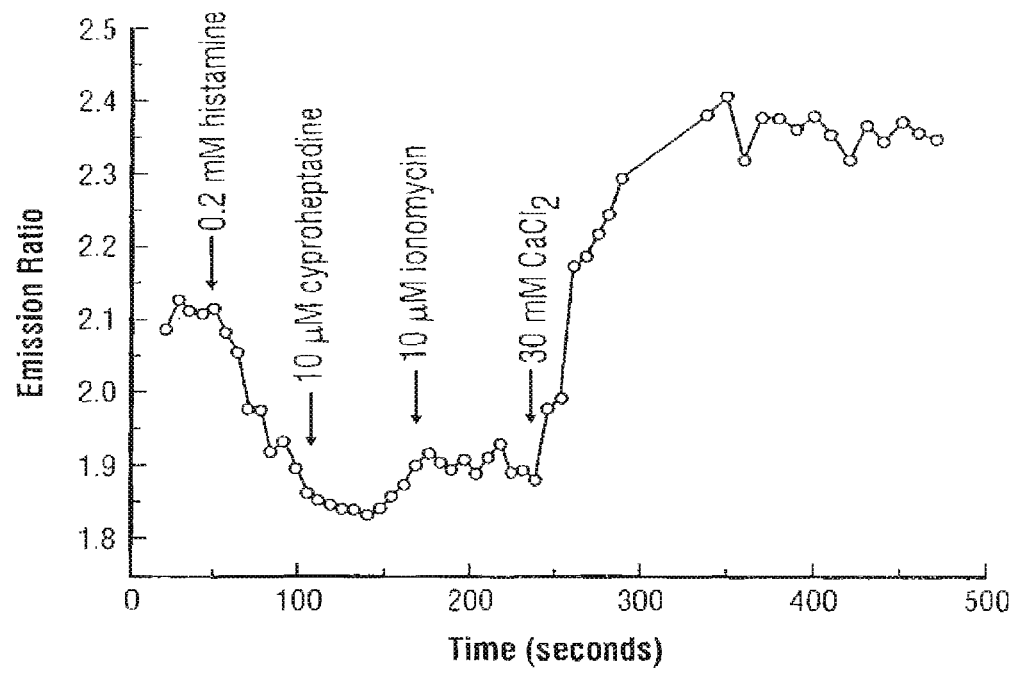
FIG. 6f is a graph depicting the time-course of emission ratio of cameleon-3er (average of four cells).

FIG. 6f shows a time course of the average $Ca^{2+}_{er}$ concentration of four cells obtained with a video-rate confocal microscope. Digital fluorescence images were the result of simultaneous acquisition of two confocal single-wavelength emission images at 450 nm (65 nm bandpass) and 535 nm (45 nm bandpass). After background subtraction, the ratio of the long wavelength image over the short wavelength one was calculated. Cells were illuminated for 66 msec (2 frames) for each time point. The interference filters and dichroics, and the sensitivity of the detectors are different between the CCD and confocal microscope systems. Therefore, the ratios obtained in the two systems differ quantitatively.

The pre-stimulus $Ca^{2+}_{er}$ concentration reported by cameleon-3er was consistently higher than cytosolic or nuclear $Ca^{2+}$ concentrations reported by cameleon-2 and cameleon-2nu, respectively. Histamine reproducibly decreased the $Ca^{2+}$, concentration in all of 15 cells, whereas it always increased the cytosolic and nuclear $Ca^{2+}$ concentrations. Receptor blockade by cyproheptadine reversed the decrease $Ca^{2+}$, concentration, indicating refill of the $Ca^{2+}$ pools. In FIG. 6f, the ratio did not reach the value of the resting state, whereas complete reversion was observed in five other experiments. Addition of ionomycin and 20 mM extracellular $Ca^{2+}$ increased $Ca^{2+}$, concentration to a saturating value above the starting level. Changes in $Ca^{2+}_{er}$ concentration were generally slower than those of the cytosol and nuclei.

The targetability of the fluorescent indicators can permit $Ca^{2+}$ measurements at previously inaccessible sites such as the immediate vicinity of synaptic vesicles or $Ca^{2+}$ channels, and in genetically tractable organisms that do not load well with esters of small-molecule indicators.

The Examples described below are illustrative of the disclosed method; however, many alternatives, modifications and variations will be clear to those skilled in the art.

EXAMPLES

Gene Construction

The cDNA of the GFP mutant P4-3 was amplified by PCR with a sense primer containing a BamHI site, and a reverse primer containing an SphI site and eliminating the GFP stop codon. See, for example, Heim, R. & Tsien, R. Y. Current Biol. 6:178-182 (1996). Likewise, the cDNA of S65T was amplified with a Sad site and an EcoRI site introduced to the 5' and 3' ends of the gene, respectively. Two restriction sites (SphI and Sad) were introduced by PCR into 5' and 3' ends of the CaM-M13 gene, respectively, using the pHY1 as a template. See, Porumb, T., et al. Prot. Engineering 7:109-115 (1994). All the amplification reactions were done by Pfu polymerase (Stratagene). The restricted products were ligated and cloned in-frame into the BamHI/EcoRI sites of pRSETB (Invitrogen). The modifications of the boundary regions between P4-3 and CaM and between M13 and S65T were performed by PCR or by a combined use of restriction enzymes, Klenow fragment of DNA polymerase I, T4 DNA polymerase, mung bean exonuclease, and T4 DNA ligase as described, for example, in Molecular Cloning, A Laboratory Manual (eds. Sambrook, J., Fritsch, E. F. & Maniatis, T.) (CSH Laboratory Press, 1989). The phEGFP plasmid was commercially available from Clontech. Two amino acid substitutions (Y66H and Y145F) were made in hEGFP to construct EBFP. oligonucleotide-directed mutageneses were carried out using the Muta-Gene Phagemid in vitro kit (Bio-Rad) at the codons for Y66H and Y145F of EGFP, and for E104Q of the calmodulin. The 5' end of the EBFP gene was modified by PCR to have a HindIII restriction site followed by a Kozak's consensus sequence. The HindIII/EcoRI fragment encoding the entire chimeric protein was subcloned in the mammalian expression vector pcDNA3 (Invitrogen).

For cameleon-2nu, the cameleon-2 DNA was extended by PCR at the 3' end with the sequence encoding the nuclear localization sequence (PKKKRKVEDP) (SEQ. ID. NO.: 55).

See, Forbes, D. J. Ann Rev. Cell Biol. 8:495-527 (1992). Cameleon-3er DNA was likewise obtained by extending the cameleon-3 DNA at the 5' end with the sequence encoding the localization sequence peptide from calreticulin (MLLPV-PLLLGLLGLAAAD) (SEQ. ID. NO.: 56), and at the 3' end with the sequence encoding the ER retention signal (KDEL). See, Kendall, J. M. et al., Biochem. Biophys. Res. Commun. 189:1008-1016 (1992).

Protein Expression and Spectroscopy

The expression of chimera proteins in bacteria was performed using the T7 expression system (pRSETB/JM109 (DE3)). Cultures were grown at room temperature, and protein expression was induced by isopropyl B-D-thiogalactoside. Cells were lysed by a French press. The polyhistidine-tagged chimera proteins were purified from the cleared lysates on nickel-chelate columns (Qiagen). The protein samples in the eluates were concentrated by Centricon 30 (Amicon), and were further purified by gel-filtration column to remove abortive chimera proteins which resulted from proteolysis or misfolding. Emission spectra of the purified proteins were measured using a fluorometer (Spex Industries, Edison, N.J.) at excitation 380 nm.

$Ca^{2+}$ Titration and Calibration

The titration experiments were performed by the "pH-metric method" as described in Grzegorz, G., et al., J. Biol. Chem. 260:3440-3450 (1985). In situ calibration for cytosolic $Ca^{2+}$ concentration utilized the equation:

$$[Ca^{2+}]c = K'_d((R-R_{min})/(R_{max}-R))^{1/nH}$$

where $K'_d$ is the apparent dissociation constant corresponding to the $Ca^{2+}$ concentration at which R is midway between $R_{max}$ and $R_{min}$, and nH is the Hill coefficient.

Imaging

Two to five days after the cDNA transfection with lipofectin (Gibco BRL), the cells were imaged on a Zeiss Axiovert microscope with a cooled CCD camera (Photometrics, Tucson, Ariz.) interfaced to a personal computer. The program MetaFluor 2.75 (Universal Imaging) was used for controlling data acquisition and analysis. Dual-emission ratio imaging was carried out by manually switching the two emission filters (440DF40 for EBFP, 535DF45 for EGFP) in front of a single imaging camera. The excitation filter (330WB80) was used with a 420DRLP dichroic mirror. Digital fluorescence imaging with a video-rate confocal microscope was performed as described in Tsien, R. Y. & Backskai, B. J. Handbook of Biological Confocal Microscopy (ed. Pawley, J. B.) (Plenum Press, New York, 1995) p. 459-478. Cells were illuminated with wide band UV (351-364 nm) from an $Ar^+$ ion laser. The primary dichroic (380DRLP) reflects UV and transmits light emitted from the specimen, which is subsequently split by a secondary dichroic (505DRLP) into two broad bands: EBFP emission (450DF65) and EGFP emission (535DF45), and counted by photomultiplier tubes.

From the above description, the essential characteristics of the present invention can be ascertained. Without departing from the spirit and scope thereof, various changes and modifications of the invention can be made to adapt it to various usages and conditions. Thus, other embodiments are also within the claims.

What is claimed is:

1. A fluorescent fusion protein indicator comprising:
   a binding protein moiety having an analyte-binding region which binds an analyte and causes the indicator to change conformation upon exposure to the analyte and wherein the binding protein moiety further includes a peptide-binding region for binding a target peptide moiety;
   a linker polypeptide moiety between about 1 amino acid residue and about 30 amino acid residues in length that links the binding protein and the target peptide moiety;
   a target peptide moiety;
   a donor fluorescent protein moiety; and an acceptor fluorescent protein moiety;
   wherein the binding protein moiety, the linker polypeptide moiety, the target peptide moiety, the donor fluorescent protein moiety, and the acceptor fluorescent protein moiety together form a single polypeptide chain in which one of the donor fluorescent protein moiety or the acceptor fluorescent protein moiety is located at the carboxy terminus of the single polypeptide chain and the other of the donor fluorescent protein moiety or the acceptor fluorescent protein moiety is located at the amino terminus of the single polypeptide chain; and
   wherein the donor fluorescent protein moiety and the acceptor fluorescent protein moiety change position relative to each other when the analyte binds to the analyte-binding region, altering fluorescence resonance energy transfer between the donor fluorescent protein moiety and the acceptor fluorescent protein moiety when the donor fluorescent protein moiety and the acceptor fluorescent protein moiety when the donor fluorescent protein moiety is excited and the donor fluorescent protein moiety and the acceptor fluorescent protein moiety are *Aequorea*-related or *Renilla*-related fluorescent protein moieties.

2. The indicator of claim 1, wherein the acceptor and donor fluorescent protein moieties are each at least 95% identical over a length of 200 contiguous amino acids to a wild-type *Aequorea*-related fluorescent protein over a length of 200 contiguous amino acids.

3. The indicator of claim 2, wherein the acceptor fluorescent protein moiety is located at the carboxy terminus of the indicator and the donor fluorescent protein moiety is located at the amino terminus of the indicator.

4. The indicator of claim 2, wherein the indicator further comprises a localization sequence.

5. The indicator of claim 4, wherein the localization sequence is a nuclear localization sequence, an endoplasmic reticulum localization sequence, a peroxisome localization sequence, a mitochondrial localization sequence, or a localized protein.

6. The indicator of claim 2, wherein the binding protein moiety is calmodulin, a calmodulin-related protein moiety, cGMP-dependent protein kinase, a steroid hormone receptor, a ligand binding domain of a steroid hormone receptor, protein kinase C, inositol-1,4,5-triphosphate receptor, or recoverin.

7. The indicator of claim 2, wherein the binding protein moiety is calmodulin or a calmodulin-related protein moiety.

8. The indicator of claim 7, wherein the donor fluorescent protein moiety is P4-3, EBFP, or W1B, and the acceptor fluorescent protein moiety is S65T, EGFP, or 10c.

9. The indicator of claim 7, wherein the target peptide moiety is a calmodulin-binding domain of skMLCKp, smMLCK, CaMKII, Caldesmon, Calspermin, phosphofructokinase calcineurin, phosphorylase kinase, Ca2+-ATPase 59 kDa PDE, 60 kDa PDE, nitric oxide synthase, type I adenylyl cylclase, *Bordetella pertussis* adenylyl cyclase, Neuromodulin, Spectrin, MARCKS, F52, β-Adducin, HSP90a, HIV-1 gp160, BBMHBI, Dilute MHC, Mastoparan, Melittin, Glucagon, Secretin, VIP, GIP, or Model Peptide CBP2.

10. The indicator of claim 9, wherein the target peptide moiety is the calmodulin-binding domain of skMLCK.

11. The indicator of claim 10, wherein the linker moiety is -Gly-Gly-.

12. The indicator of claim 7, wherein the target peptide moiety is M13.

13. A method for determining the concentration of an analyte in a sample comprising the steps of contacting the sample with a fluorescent indicator and determining the degree of fluorescence resonance energy transfer in the sample whereby the concentration of the analyte in the sample is determined;
   wherein the fluorescent indicator comprises:
   a binding protein moiety having an analyte-binding region which binds an analyte and causes the indicator to change conformation upon exposure to the analyte and wherein the binding protein moiety further includes a peptide-binding region for binding a target peptide moiety;
   a linker polypeptide moiety between about 1 amino acid residue and about 30 amino acid residues in length that links the binding protein and the target peptide moiety;
   the target peptide moiety;
   a donor fluorescent protein moiety;
   and an acceptor fluorescent protein moiety; wherein the binding protein moiety, the linker polypeptide moiety, the target peptide moiety, the donor fluorescent protein moiety, and the acceptor fluorescent protein moiety form a single polypeptide chain in which one of the donor fluorescent protein moiety or the acceptor fluorescent protein moiety is located at the amino terminus of the single polypeptide chain; and wherein the donor fluorescent protein moiety and the acceptor fluorescent protein moiety change position relative to each other when the analyte binds to the analyte binds to the analyte-binding region, altering fluorescence resonance energy transfer between the donor fluorescent protein moiety and the acceptor fluorescent protein moiety when the donor fluorescent protein moiety is excited and the donor fluorescent protein moiety and the acceptor fluorescent protein moiety are *Aequorea*-related or *Renilla*-related fluorescent protein moieties.

14. The method of claim 13, wherein the step of determining the degree of fluorescence resonance energy transfer in the sample comprises measuring light emitted the acceptor fluorescent protein moiety.

15. The method of claim 13, wherein the step of determining the degree of fluorescence resonance energy transfer in the sample comprises measuring light emitted from the donor fluorescent protein moiety, measuring light emitted from the acceptor fluorescent protein moiety, and calculating a ratio of the light emitted from the donor fluorescent protein moiety and the light emitted from the acceptor fluorescent protein moiety.

16. The method of claim 13, wherein the step of determining the degree of fluorescence resonance energy transfer in the sample comprises measuring the excited state lifetime of the donor moiety.

17. The method of claim 15, further comprising the steps of determining the concentration of the analyte at a first time after contacting the sample with the fluorescence indicator, determining the concentration of the analyte at a second time after contacting the sample with the fluorescence indicator, and calculating the difference in the concentration of the analyte at the first time and the second time, whereby the difference in the concentration of the analyte in the sample reflects a change in concentration of the analyte present in the sample.

18. The method of claim 17, further comprising the step of contacting the sample with a compound between the first time and the second time, whereby a difference in the concentration of the analyte in the sample between the first time and the second time indicates that the compound alters the presence of the analyte.

19. The method of claim 13, wherein the sample comprises an intact cell and the contacting step comprises incorporating the fluorescent indicator into the cell.

20. The method of claim 19, wherein step of incorporating the fluorescent indicator into the cell includes transfecting the cell with an expression vector comprising expression control sequences operably linked to a nucleic acid sequence coding for the expression of the fluorescent indicator.

21. The method of claim 13, wherein the analyte is calcium.

22. The method of claim 13, wherein the donor fluorescent protein moiety and the acceptor fluorescent protein moiety are *Aequorea*-related fluorescent protein moieties and wherein the acceptor fluorescent protein moiety is located at the carboxy terminus of the indicator and the donor fluorescent protein moiety is located at the amino terminus of the indicator.

* * * * *